US011879890B1

(12) United States Patent
Verbeck, IV et al.

(10) Patent No.: US 11,879,890 B1
(45) Date of Patent: *Jan. 23, 2024

(54) TECHNIQUES FOR RAPID DETECTION AND QUANTITATION OF VOLATILE ORGANIC COMPOUNDS (VOCS) USING BREATH SAMPLES

(71) Applicants: InspectIR Systems, LLC, Frisco, TX (US); University of North Texas, Denton, TX (US)

(72) Inventors: Guido Fridolin Verbeck, IV, Lewisville, TX (US); John Redmond, Frisco, TX (US); Tim C. Wing, Frisco, TX (US); Luke Keiser, Frisco, TX (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/033,581

(22) Filed: Sep. 25, 2020

Related U.S. Application Data

(63) Continuation-in-part of application No. 16/715,576, filed on Dec. 16, 2019, now Pat. No. 10,813,585.
(Continued)

(51) Int. Cl.
  G01N 33/497 (2006.01)
  A61B 5/097 (2006.01)
  (Continued)

(52) U.S. Cl.
  CPC ........... G01N 33/497 (2013.01); A61B 5/082 (2013.01); A61B 5/097 (2013.01); A61B 5/4845 (2013.01);
  (Continued)

(58) Field of Classification Search
  CPC .... G01N 33/497; G01N 1/2247; G01N 21/39; G01N 27/624; G01N 30/72;
  (Continued)

(56) References Cited

U.S. PATENT DOCUMENTS

| 3,896,661 A | * | 7/1975 | Parkhurst | G01N 30/95 |
| | | | | 250/288 |
| 5,479,815 A | | 1/1996 | White et al. | |

(Continued)

FOREIGN PATENT DOCUMENTS

| CN | 105263415 A | * | 1/2016 | ........... A61B 3/0008 |
| CN | 106769719 A | | 5/2017 | |

(Continued)

OTHER PUBLICATIONS

International Search Authority (ISA), "International Search Report," International Application No. PCT/IB2019/056456, dated Dec. 20, 2019, 2 pages, publisher Commissioner for Patents—PCT, Alexandria, Virginia, United States of America.
(Continued)

*Primary Examiner* — Marrit Eyassu
(74) *Attorney, Agent, or Firm* — Fogarty LLP

(57) ABSTRACT

An exemplary breath analysis system may include a sampling chamber having a molecule collector disposed therein. The molecule collector may be configured such that volatile organic compounds (VOCs) present in a breath sample introduced to the sampling chamber adhere to the molecule collector. A laser may be configured to ablate at least a portion of the VOCs adhered to the molecule collector off of the molecule collector to release of at least the portion of the VOCs adhered to the molecule collector. An analysis device (e.g., a mass spectrometer or Terahertz (THz) spectrometer) may identify one or more target VOCs from among at least the portion of the VOCs released from the molecule collector and generate an output representative of the identified target VOC(s). The output may include information that quantitates a concentration of the target VOC(s) with respect to a source of the breath sample.

22 Claims, 16 Drawing Sheets

Related U.S. Application Data which is a continuation of application No. PCT/IB2019/056456, filed on Jul. 29, 2019.

(60) Provisional application No. 62/712,941, filed on Jul. 31, 2018.

(51) Int. Cl.
*A61B 5/08* (2006.01)
*G01N 33/94* (2006.01)
*A61B 5/00* (2006.01)

(52) U.S. Cl.
CPC ....... *G01N 33/948* (2013.01); *G01N 33/9486* (2013.01); *G01N 2033/4975* (2013.01)

(58) Field of Classification Search
CPC ............. G01N 33/948; G01N 33/9486; G01N 2021/392; G01N 2021/396; G01N 2033/4975; G01N 2560/00
USPC ........................................................ 73/23.23
See application file for complete search history.

(56) References Cited

U.S. PATENT DOCUMENTS

| | | | | |
|---|---|---|---|---|
| 5,728,584 A | * | 3/1998 | Sausa | G01N 21/631 |
| | | | | 73/35.14 |
| 6,248,078 B1 | | 6/2001 | Risby et al. | |
| 7,299,711 B1 | | 11/2007 | Linker et al. | |
| 7,388,195 B2 | | 6/2008 | Zapata et al. | |
| 8,237,118 B2 | | 8/2012 | Prox et al. | |
| 8,288,727 B2 | | 10/2012 | Cormier et al. | |
| 8,759,791 B1 | * | 6/2014 | Hug | G01N 21/645 |
| | | | | 250/282 |
| 8,784,737 B2 | | 7/2014 | Rafferty et al. | |
| 9,315,848 B2 | | 4/2016 | Haick et al. | |
| 9,398,881 B2 | | 7/2016 | Davis et al. | |
| 9,733,225 B2 | | 8/2017 | Armstrong | |
| 10,067,119 B2 | | 9/2018 | Davis et al. | |
| 10,111,606 B2 | | 10/2018 | Davis et al. | |
| 10,520,439 B2 | | 12/2019 | Palmskog et al. | |
| 11,033,203 B2 | | 6/2021 | Allsworth et al. | |
| 2003/0116705 A1 | | 6/2003 | Kanik et al. | |
| 2005/0051719 A1 | | 3/2005 | Miller et al. | |
| 2005/0054942 A1 | | 3/2005 | Melker et al. | |
| 2005/0065446 A1 | | 3/2005 | Talton | |
| 2006/0200037 A1 | | 9/2006 | Falasco | |
| 2006/0217626 A1 | | 9/2006 | Patel et al. | |
| 2007/0224128 A1 | | 9/2007 | Dennis et al. | |
| 2008/0268548 A1 | * | 10/2008 | Zuckerman | G01N 21/658 |
| | | | | 436/172 |
| 2011/0127421 A1 | | 6/2011 | Finlay | |
| 2012/0223226 A1 | | 9/2012 | Rafferty et al. | |
| 2012/0302907 A1 | | 11/2012 | Palmskog et al. | |
| 2013/0059319 A1 | * | 3/2013 | Erbeldinger | G01N 15/0606 |
| | | | | 435/20 |
| 2013/0211211 A1 | | 8/2013 | Sato | |
| 2014/0127326 A1 | * | 5/2014 | Sood | G01N 1/405 |
| | | | | 73/23.3 |
| 2014/0288454 A1 | | 9/2014 | Paz et al. | |
| 2015/0260706 A1 | | 9/2015 | Killard et al. | |
| 2015/0289782 A1 | | 10/2015 | Peverall et al. | |
| 2015/0305651 A1 | | 10/2015 | Attariwala et al. | |
| 2016/0054294 A1 | * | 2/2016 | Rihani | G01N 21/6486 |
| | | | | 73/23.3 |
| 2016/0054295 A1 | | 2/2016 | Grisel et al. | |
| 2016/0299125 A1 | | 10/2016 | Cristoni et al. | |
| 2016/0363582 A1 | | 12/2016 | Blackley | |
| 2017/0023453 A1 | * | 1/2017 | Hill, Jr. | G01N 1/4022 |
| 2017/0074857 A1 | | 3/2017 | Dennis et al. | |
| 2017/0107556 A1 | | 4/2017 | Koo et al. | |
| 2017/0143933 A1 | | 5/2017 | Pasadilla et al. | |
| 2017/0191910 A1 | | 7/2017 | Laskowski et al. | |
| 2018/0056302 A1 | | 3/2018 | Ahmad et al. | |
| 2018/0100862 A1 | | 4/2018 | Goix et al. | |
| 2018/0146886 A1 | | 5/2018 | Leard et al. | |
| 2018/0214050 A1 | * | 8/2018 | Purves | G01N 33/004 |
| 2018/0306775 A1 | | 10/2018 | Beck et al. | |
| 2020/0029858 A1 | | 1/2020 | Reddy | |

FOREIGN PATENT DOCUMENTS

| | | |
|---|---|---|
| EP | 2475977 B1 | 6/2015 |
| JP | H09281040 A | 10/1997 |
| JP | 2013504074 A | 2/2013 |
| WO | 2006060130 A2 | 6/2006 |
| WO | 2010031788 A1 | 3/2010 |
| WO | 2011029888 A1 | 3/2011 |
| WO | 2011029889 A1 | 3/2011 |
| WO | 2014029663 A1 | 2/2014 |
| WO | 2017091134 A1 | 6/2017 |

OTHER PUBLICATIONS

International Search Authority (ISA), "Written Opinion of the International Searching Authority," International Application No. PCT/IB2019/056456, dated Dec. 20, 2019, 6 pages, publisher Commissioner for Patents—PCT, Alexandria, Virginia, United States of America.

International Preliminary Report on Patentability, dated Feb. 11, 2021, 8 pages, publisher the International Bureau of WIPO, Geneva, Switzerland.

European Patent Office, Extended European Search Report issued for European Patent Application No. 19844255.0, dated Mar. 2, 2022, 7 pages.

Government of India, Intellectual Property Office, Examination Report issued for Indian Patent Aoolication No. 202117006438, dated Apr. 18, 2023, 7 pages.

Australian Government, IP Australia, Examination Report issued for Australian Patent Application No. 2019316258, dated May 22, 2023, 2 pages.

Japanese Patent Office, Office Action issued for Japanese Patent Application No. 2021-529539, dated Mar. 28, 2023, 9 paqes.

* cited by examiner

TECHNIQUES FOR RAPID DETECTION AND QUANTITATION OF VOLATILE ORGANIC COMPOUNDS (VOCS) USING BREATH SAMPLES

CROSS REFERENCE TO RELATED APPLICATION

This is a continuation in part of, and claims the benefit of priority of, U.S. patent application Ser. No. 16/715,576, entitled Techniques for Rapid Detection and Quantitation of Volatile Organic Compounds (VOCS) Using Breath Samples, filed Dec. 16, 2019, and therethrough, of International Application Number PCT/IB2019/056456, also entitled Techniques for Rapid Detection and Quantitation of Volatile Organic Compounds (VOCS) Using Breath Samples, filed Jul. 29, 2019, and therethrough, of U.S. Provisional Patent Application No. 62/712,941, filed Jul. 31, 2018, each of which is hereby incorporated herein by reference, in its entirety.

TECHNICAL FIELD

The present application relates to breathalyzer systems and devices. More specifically the present application relates to breathalyzer systems and devices designed to facilitate quantitative analysis of THC and other substances in the field using breath samples.

BACKGROUND

Marijuana legalization has created many judicial issues and raises concerns of safety for civilians. Daily marijuana users have increased from 9.8% of the population of the United States in 2007, to 13.39% in 2014. While this is only a 3.6% increase, the potency of Δ-9-Tetrahydrocannabinol (Δ-9-THC), the psychoactive substance in marijuana, has also increased from 5% in 2001 to over 20% in marijuana leaves and over 60% in crude extracts. The increase in potency has led to an increase in crime reports for the local population. Specifically, areas with a high density of marijuana dispensaries had higher rates of property crime among all states with dispensaries. Another problem with marijuana legalization is the influence of marijuana while operating an automobile. Marijuana users are 25% more likely to be in an automobile accident than a sober driver, and more than 10% of all drivers on the weekend are under the influence of an illegal drug. As marijuana becomes legalized in more states, proper quantitation of Δ-9-THC is required, such that an accurate and rapid determination of whether a person is under the influence of marijuana can be achieved. This will also aid the judicial system in having a device that can accurately determine a concentration, allowing a set limit of Δ-9-THC to be determined for operating a vehicle.

Three cannabinoid compounds are currently analyzed to determine cannabinoid concentrations in the blood; they are Δ-9-THC, 11-hydroxytetrahydrocannabinol (11-OH-THC), and carboxy-tetrahydrocannabinol (THC-COOH). Currently, techniques for determining the presence of drugs, such as cannabinoids, require analysis via a blood, blood plasma, urine, or oral fluid samples. Most analytical techniques use gas chromatography coupled to mass spectrometry (GC/MS). This presents a problem of having to collect a sample and bring it back to the lab for further analysis. These techniques have a long analysis time, with most analyses taking more than 15 minutes to detect the cannabinoids. Furthermore, detecting Δ-9-THC using GC/MS can also introduce another problem because the ionization source is electron ionization (EI). Cannabidiol (CBD), an extracted resin from the hemp plant, has the same molecular weight as Δ-9-THC, as well as the same mass spectrum fragmentation patterns when ionized using electron ionization. Under the controlled substances act, CBD is classified as a Schedule I drug because of it being a derivative of marijuana. However, the agricultural act of 2014 allows industrial hemp to be cultivated and sold for purposes of marketing research. Some states view this bill as the right to contract agriculturalists to sell CBD legally. This creates a challenge in quantifying the amount of Δ-9-THC in person's breath because the signal may be a result of CBD in the person's breath, which they may have obtained legally.

Laws for legal limits of Δ-9-THC in the body have been established in some states. Twelve states have the zero-tolerance policy, which states that no person should have any cannabinoids in their blood while driving. However, five states allow the use of medical marijuana. This causes an issue for patients getting treatment and then having to drive later in the day or later in the week because they could be considered to driving under the influence of marijuana (DUIM). The analytical techniques that test for all three cannabinoids can be problematic because THC-COOH, which is not psychoactive, remains in the blood long after both Δ-9-THC and 11-OH-THC remain in the blood. A person can fail a cannabinoid test even though they are experiencing no psychoactive effects. Other states have adopted per se blood *cannabis* content (BCC) laws. These select states each have their own limit with the overall range being between 1 nanogram of THC to milliliter of blood (ng/ml) to 5 ng/ml. If the person driving has a concentration higher than those values, they are deemed DUIM, which carries similar penalties to driving while intoxicated. Unfortunately, a device that can accurately and rapidly detect Δ-9-THC concentrations has yet to be developed.

Detecting cannabinoids from the breath of a person is needed to allow a non-invasive rapid determination in the field. Previous methods of breath determination of cannabinoids originate back to 1972, when marijuana was detected in the breath of people under the influence using a colorimetric test. This test collected breath and used a series of reactions with quinone-4-haloimine, 2,6-dihaloquinone-4-haloimine, sodium hydroxide, and ammonia to determine if the breath sample would change to a blue or red color. These colorimetric tests had to be done in large reaction vessels, had a broad range of colors representing a positive result, and required at least 1 microgram of THC in the breath to have a positive reaction. These tests were not capable of quantitating the level of Δ-9-THC, nor were they able to be used in the field.

Currently, three types of breathalyzers are being used by local law enforcement officers in the field, liquid chromatography coupled to mass spectrometry (LC/MS), high-field asymmetric waveform ion mobility (FAIMS), and liquid chromatography coupled to spectroscopy. A first company, Sensabues, utilizes a breath sampling kit. The person breathes into the sampling chamber and then the apparatus is sent back to the lab to be analyzed using LC/MS. While this method is useful for quantitation, it cannot be used in the field, which hinders this method. In addition, LCMS requires several minutes to analyze the sample once it has reached the lab before the cannabinoids can be seen. Two other companies provide systems that are capable of in field measurements. Cannabix Technologies Inc. has worked with the Yost research group at University of Florida to create a portable breathalyzer for Δ-9-THC that utilizes high-field asymmetric waveform ion mobility spectrometry (FAIMS). This device can analyze samples in a two-minute time window and can detect and quantitate Δ-9-THC in the sample at concentrations of 10 parts per million (ppm). While this device overcomes the portability issue, FAIMS does not contain the same resolution or peak capacity that is necessary for determining the concentration of Δ-9-THC. Without the proper resolution, the instrument would not be able to distinguish the compounds of tobacco smoke from *cannabis* smoke. Furthermore, without the peak capacity, other compounds, such as illicit drugs may be overlooked, allowing the driver to continue driving while under the influence of a different illicit substance. Another company, Hound Labs Inc., has developed a handheld instrument that also utilizes liquid chromatography coupled to spectroscopy to detect for the presence of Δ-9-THC by linking a fluorescent adduct to the para-position of the Δ-9-THC molecule. This device only requires picogram quantities of Δ-9-THC and works by capturing the breath of the person and condensing the breath onto C18 media. The media is then delivered to a TLC plate, where a solvent mixture is administered and after several minutes the fluorescent label is placed on the entire TLC plate. The fluorescent label will bind specifically to the Δ-9-THC, which is then excited using a diode-pumped solid-state laser. This excited state will cause a shift in the spectrum and can be referenced to a known Δ-9-THC sample. This method requires more than 8 minutes to analyze a sample and requires the use of a known reference every time an analysis takes place.

Since the turn of the century the number of synthetic opioid overdoses of civilians have risen 200% and from the years 2014-2016 50% of all drug overdoses were attributed to opioids. Military personnel have also had an increase in opioid overdoses as military emergency departments have recorded a steady rise of opioid overdoses increasing from 27% to 42% during the years of 2009-2012. With so many opioid overdoses occurring among both civilians and military personnel a need for improved detection methods is warranted. Most drug enforcement agencies can only analyze the opioid using gas chromatography coupled to mass spectrometry (GC/MS) or liquid chromatography to mass spectrometry (LC/MS). Opioids such as methadone and fentanyl are immediately hydroxylated upon entering the human body. This process of hydroxylation begins a metabolic cycle that creates volatile organic compounds (VOCs) such as propionic acid. Previous methods used to detect these VOCs have been with solid phase micro extraction (SPME) techniques coupled to GC/MS. Unfortunately, these methods require long equilibration times of up to 10 minutes

SUMMARY

Systems, apparatuses, methods, and computer-readable storage media providing techniques for improved on-site quantitation of cannabinoids and other substances from breath samples are disclosed. Exemplary breath analysis systems and apparatuses of the present disclosure may include a sampling chamber having an inlet configured to receive a breath sample and provide the breath sample to the sampling chamber. A molecule collector may be disposed within the sampling chamber. The molecule collector may be configured such that volatile organic compounds (VOCs) present in the breath sample introduced to the sampling chamber adhere to the molecule collector. The breath analysis systems and apparatuses may include a laser configured to ablate at least a portion of the VOCs adhered to the molecule collector off of the molecule collector to cause resorption those VOCs. The exemplary breath analysis systems and apparatuses may include an analysis device configured to identify one or more target VOCs from among at least the portion of the VOCs released from the molecule collector and generate an output representative of the identified one or more target VOCs. The output may include information that quantitates a concentration of the one or more target VOCs with respect to a source of the breath sample with respect to the breath sample provided to the sampling chamber. In aspects, the analysis device may identify the one or more target VOCs using a mass spectrometer or Terahertz (THz) spectrometer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1A:
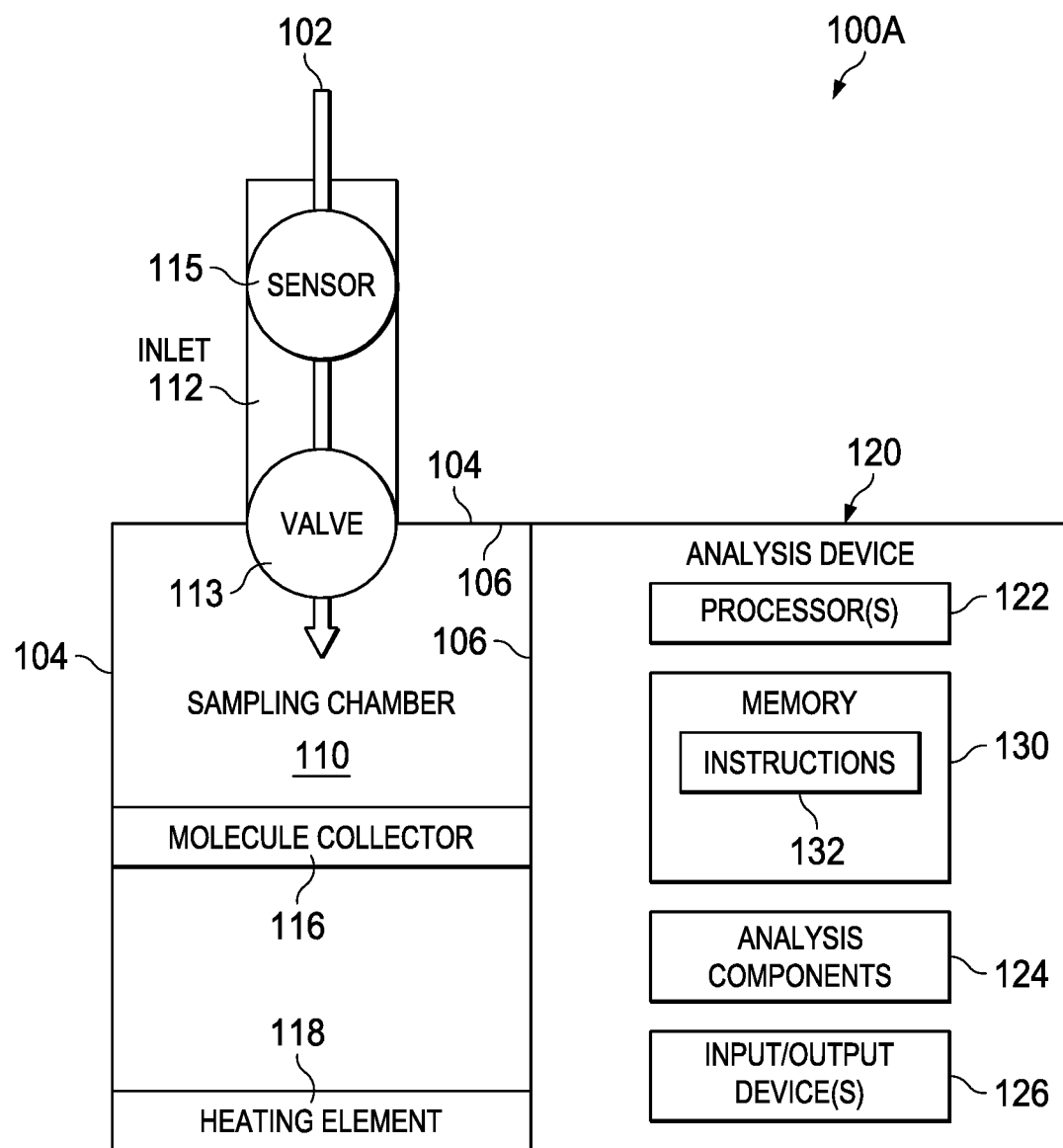
FIG. 1A illustrates a block diagram of a system for analyzing breath samples in accordance with aspects of the present disclosure.

Referring to FIG. 1A, a block diagram of a system for analyzing breath samples in accordance with aspects of the present disclosure is shown as a system 100A. As shown in FIG. 1A, the system 100A includes a sampling chamber 110 and an analysis device 120. In aspects, the sampling chamber 110 may be configured as a removable and/or disposable component of the system 100A. In such an arrangement, the sampling chamber 110 may be removably coupled to the analysis device 120. Configuring the sampling chamber 110 as a removable component of the system 100A may prevent contamination of consecutive breath samples analyzed by the analysis device 120. For example, a first sampling chamber may be utilized to perform analysis of a breath sample provided by a first person and a second sampling chamber may be utilized to perform analysis of a breath sample provided by a second person. Using different sampling chambers for different breath samples prevents one breath sample from potentially contaminating another breath sample. Where the sampling chamber(s) 110 is configured as a disposable component, the sampling chamber may be discarded after use or after a desired time has elapsed, such as an amount of time required by a law enforcement agency to retain the sampling chamber (e.g., for evidentiary purposes). Where the sampling chamber(s) 110 is configured as a reusable component, the sampling chamber 110 may be cleaned and prepared for subsequent reuse as needed. In aspects, a portion of the analysis device 120 may also be configured as a disposable and/or reusable component, such as portions of the analysis device 120 that may become contaminated if utilized to analyze multiple breath samples. In an aspect, the sampling chamber may be configured as a cartridge that may be utilized to obtain a breath sample and then placed within or coupled to the sampling device 120 for analysis. For example, the analysis device 120 may be installed in a law enforcement vehicle and a law enforcement official may have a person suspected of DUIM provide a breath sample to the cartridge, and then couple the cartridge to the analysis device 120 to facilitate analysis in accordance with aspect of the present disclosure. It is noted that the exemplary configurations described above have been provided for purposes of illustration, rather than by way of limitation and that numerous other ways for arranging, coupling, and/or integrating components of breath analysis systems in accordance with the present disclosure may be utilized.

As shown in FIG. 1A, the sampling chamber 110 may comprise a housing having an outer surface 104 and an inner surface 106. The inner surface 106 of the housing may define a volume of the sampling chamber. An inlet 112 may be coupled to the sampling chamber 110. The inlet 112 may be configured to receive a breath sample 102 and to provide the breath sample 102 to the sampling chamber 110, and more specifically to provide the breath sample 102 to the volume of the sampling chamber. In aspects, a disposable mouthpiece (not shown in FIG. 1A) may be removably coupled to a first end of the inlet 112 and a second end of the inlet 112 may be coupled to the sampling chamber 110. Alternatively, the first end of the inlet 112 may be utilized as the mouthpiece and the second end of the inlet 112 may be coupled to the sampling chamber 110. A valve 113 may be disposed within an air flow path between the inlet 112 and the sampling chamber 110. The valve 113 may be configurable to at least a first state and a second state. The first state may correspond to an open state configured to allow the breath sample 102 to flow into the sampling chamber 110 and the second state may correspond to a closed state configured to prevent contamination of the breath sample 102, such as by preventing ambient air from entering the sampling chamber 110 once the breath sample 102 has been provided. In an aspect, the sampling chamber 110 may include an outlet configured to release non-VOCs from the sampling chamber 110, as illustrated and described below with reference to FIG. 4A. The system 100A may also include a sensor 115 configured to determine whether the breath sample satisfies one or more criterion. For example, the sensor 115 may be configured to determine whether the breath sample 102 was exerted with sufficient force, has sufficient volume, etc., which may ensure that the breath sample 102 is sufficient for facilitating analysis in accordance with aspects of the present disclosure.

A molecule collector 116 may disposed within the sampling chamber 110. At least a portion of the molecule collector 116 may be disposed within the volume of the sampling chamber 110. The molecule collector 116 may be configured to adhere to volatile organic compounds (VOCs) present in the breath sample. For example, the molecule collector 116 may be constructed of materials such as Carboxen®. It is noted that the molecule collector 116 may be formed from a single material (e.g., one of the above-described materials), or may be formed from multiple materials, such as a base material that has been coated with one or more of the above-described materials. In aspects, the molecule collector 116 may have a solid form factor, such as a plate or rod formed from the materials mentioned above, or may have another form factor, such as a mesh formed from the materials mentioned above. The sampling device 110 may also include or be coupled to a heating mechanism such as heating element 118 configured to introduce heat within the sampling chamber 110. For example, the heating mechanism 118 may include a power source coupled to the molecule collector 116 and configured to apply a voltage to the molecule collector 116. Applying the voltage to the molecule collector 116 may heat up the molecule collector, thereby introducing heat within the sampling chamber 110. As described in more detail below, the heat introduced within the sampling chamber 110 may cause the VOCs adhered to the molecule collector 116 to be released within the volume of the sampling chamber, thereby facilitating analysis and identification of one or more of the VOCs present within the sampling chamber 110.

Likewise, in accordance with various embodiments of the present systems and methods heating mechanism 118 may alternatively be a laser, photodiode array, or the like. For example, in accordance with various embodiments of the present systems and methods heating mechanism 118, may, rather than an electric heating element, be a laser configured to ablate VOCs off of molecule collector 116, such as to ablate VOCs off of a Carboxen coated mesh molecule collector, or the like. Alternatively, heating mechanism 118 may be a photodiode array configured to excite and/or heat molecule collector 116, such as a Carboxen coated mesh molecule collector, across a (visible or non-visible light) spectrum and/or over time, to stage release of VOCs off of the (Carboxen coated mesh) molecule collector.

The system 100A may include an analysis device. The analysis device 120 may be configured to identify one or more target VOCs from among the VOCs present in the sampling chamber 110 subsequent to release of at least a portion of the VOCs from the molecule collector 116 (e.g., due to the heat provided or introduced by the heating mechanism 118). Additionally, the analysis device 120 may be configured to generate an output representative of the one or more target VOCs. As shown in FIG. 1A, the analysis device 120 may include one or more processors 122, a memory 130, analysis components 124, and one or more input/output (I/O) devices 126. The memory 130 may store instructions 132 that, when executed by the one or more processors 122, cause the one or more processors 122 to control operations of the analysis device 120 and possibly other components of the system 100A, such as the heating mechanism 118, with respect to analyzing and identifying one or more target VOCs of the breath sample 102. The one or more target VOCs may include Δ-9-Tetrahydrocannabinol (Δ-9-THC), THC metabolites, opioids, opioid metabolites, or a combination thereof. Additionally, or alternatively, the one or more target VOCs may include metabolites, metabolite markers, or a combination thereof indicative of a particular disease and/or identification of a particular disease. For example, ketones and aldehydes (VOC's) that are relatively unique to a particular viral infection (e.g., COVID-19, influenza, rhinovirus, etc.), bacterial infection, or the like. Hence, in accordance with some example embodiments of the present systems and methods, the output may be representative of one or more target VOCs comprising metabolites, metabolite markers, or a combination thereof indicative of such disease(s), such as SARS-CoV-2 and/or Coronavirus Disease 2019 (COVID-19) caused by SARS-CoV-2.

The I/O devices 126 may include switches, buttons, lights, display devices, or other control elements configured to receive inputs and/or provide outputs in connection with operation of the system 100A. For example, switches and/or buttons may be provided to power the system 100A on and off, indicate that a breath sample has been provided, identify one or more target VOCs to be identified, or other functionality and control features. Lights may be provided to indicate: the system 100A is powered on or off, indicate whether the breath sample provided is satisfactory (e.g., based on information received from the sensor 115), indicate the identified VOCs (e.g., different lights may be associated with different VOCs that may be identified by the system 100A), or to provide other information associated with operation of the system 100A. One or more display devices may additionally be provided to display information, such as to indicate the identified VOCs, indicate an operational state of the system 100A (e.g., provide information indicating one or more of the different features described above with respect to the lights or other status information), and the like. The analysis component 124 may include a mass spectrometer or a Terahertz (THz) spectrometer configured to identify the one or more target VOCs of the breath sample 102.

Also, in accordance with various embodiments of the present systems and methods heating mechanism 118, may, rather than an electric heating element, be a laser configured to ablate VOCs off of molecule collector 116, such as to ablate VOCs off of a Carboxen coated mesh molecule collector. Alternatively, heating mechanism 118 may be a photodiode array configured to excite and/or heat molecule collector 116, such as a Carboxen coated mesh molecule collector, across a (visible or non-visible light) spectrum and/or over time, to stage release of VOCs off of the (Carboxen coated mesh) molecule collector.

In accordance with various embodiments of the present systems and methods heating mechanism 118 may introduce heat, and/or heat the breath sample, within the sampling chamber by ramping this heat, and/or heat of the breath sample, exciting and/or releasing lighter and/or less bound VOCs first and then exciting and/or releasing heavier and/or more strongly bound (relative to the less bound) VOCs later (or last). In such embodiments the target VOC(s) may be identified, by analysis device 120, from among the VOCs present in the sampling chamber subsequent to release of at least a portion of the VOCs from the molecule collector, by first identifying one or more lighter and/or less bound target VOCs released first, and later identifying one or more heavier and/or more strongly bound target VOCs released later from the molecule collector by ramping heat, and/or heat of the breath sample within the sampling chamber.

To provide such ramping of heat, and/or heat of the breath sample, within the sampling chamber, where the heating mechanism is a heating element that employs a power source coupled to the molecule collector. The power source voltage to the molecule collector may be ramped to ramp heat within the sampling chamber.

Figure 1B:
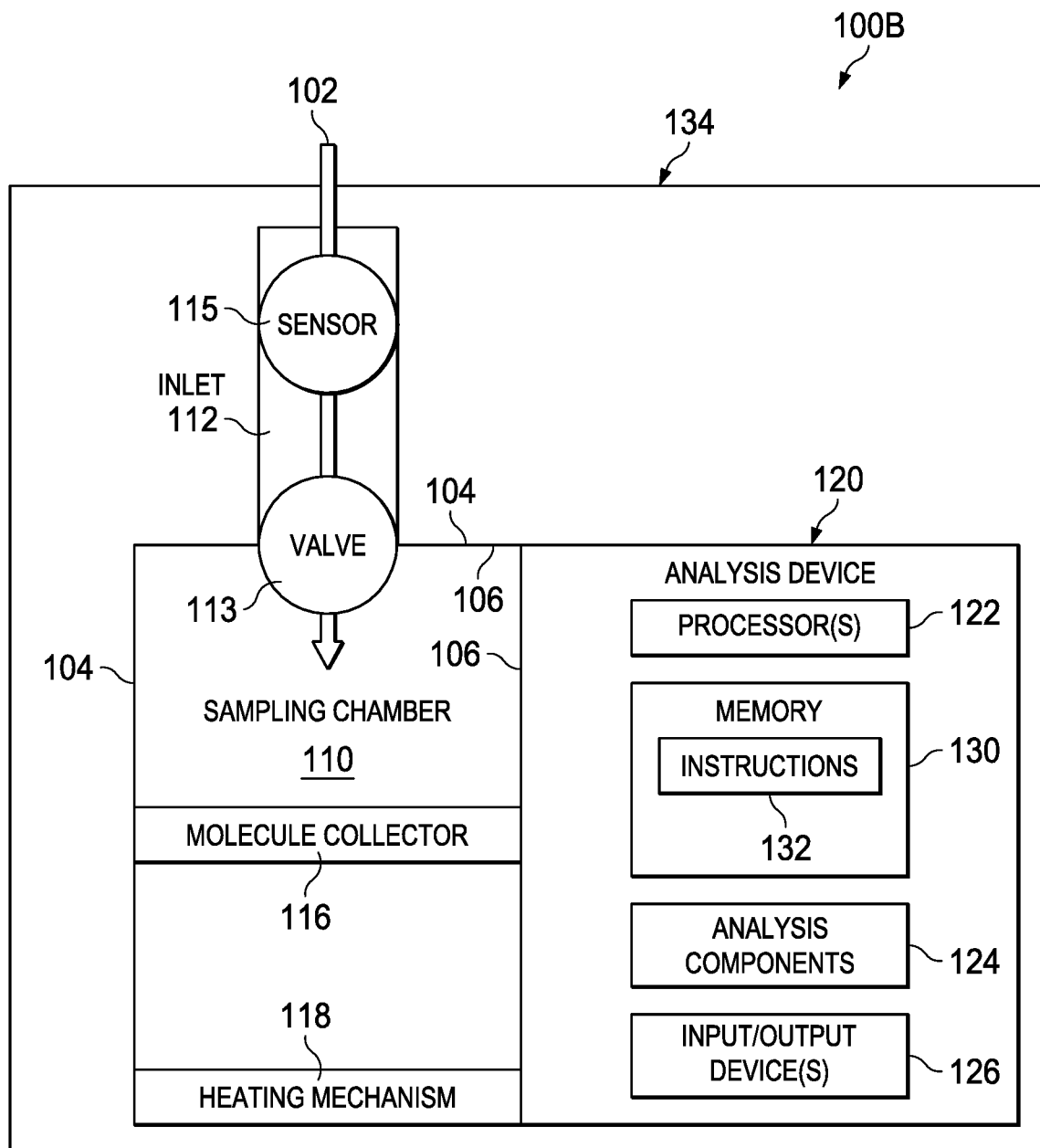
FIG. 1B is a block diagram of a system for analyzing breath samples, housed in a single portable case, or the like, in accordance with aspects of the present disclosure.

Embodiments of the present system for analyzing breath samples in accordance with aspects of the present disclosure may be housed with a single housing, such as a suitcase or briefcase-like hard case, or similar protective utility case, such as may have a carry handle, weatherproof seals, and/or the like. FIG. 1B is a block diagram of portable system 100B for analyzing breath samples, housed in a single portable case, or the like, 134 in accordance with aspects of the present disclosure. Portable system 100B is a device for analyzing a breath sample housed in portable housing 134. As noted, housing 134 may be a hard case or similar protective utility case. Housing 134 may have a carry handle, weatherproof seals between a body and lid of the case, and/or the like. Housing 134 may be made primarily from metal (such as aluminum) or from a durable material such as polypropylene.

In accordance with such embodiments sampling chamber 110 may be disposed within the portable housing, with inlet 112, operatively coupled to the sampling chamber and deployable from portable housing 134, and configured to receive a breath sample and to provide the breath sample to the sampling chamber, within housing 134. Molecule collector 116 is disposed within the sampling chamber, and thereby, likewise, in such embodiments, within housing 134, as is heating mechanism 118 (which, as noted, in accordance with embodiments of the present systems and methods may be a heating element, laser, photodiode array, or the like. Consistent with the above, valve 113 disposed in an air flow path between the inlet and the sampling chamber is disposed within portable housing 134, in accordance with such embodiments. Also, in accordance with such embodiments, sensor 115 disposed in the portable housing may be configured to determine whether the breath sample satisfies one or more criterion.

Likewise, analysis device 120 and its operative components, processor(s) 122, memory 130, analysis components 124, and input/output (I/O) device(s) 126 are disposed in case 134, in such embodiments. Power may be provided to system 100B by (rechargeable) batteries disposed in housing 134 and/or external power may be supplied into housing via a cord, external or internal (switching) power supply, or the like, from a conventional outlet or other electrical system such as the electrical system of a (law enforcement) vehicle, or the like. In accordance with the above, portable analysis system 100B may be deployed in conjunction with a law enforcement vehicle, or the like for field use, carried to a location of, such as a correctional facility, school, or other controlled-environment facility for use, and/or similarly deployed in a flexible manner, as needed.

As noted, in some embodiments, the sampling chamber may be configured as a cartridge that may be utilized to obtain a breath sample and then placed within or coupled to the sampling device 120 for analysis. For example, a law enforcement official may have a person provide a breath sample to the cartridge, and then the law enforcement official may take the cartridge to portable system 100B, such as in a law enforcement vehicle, and couple the cartridge to the analysis device 120 within housing 134 to facilitate analysis in accordance with aspect of the present disclosure. Alternatively, in some embodiments a disposable mouthpiece, extending from housing 134, may be removably coupled to a first end of inlet 112, wherein a second end of inlet 112 is coupled to the sampling chamber disposed within portable housing 134.

Figure 2A:
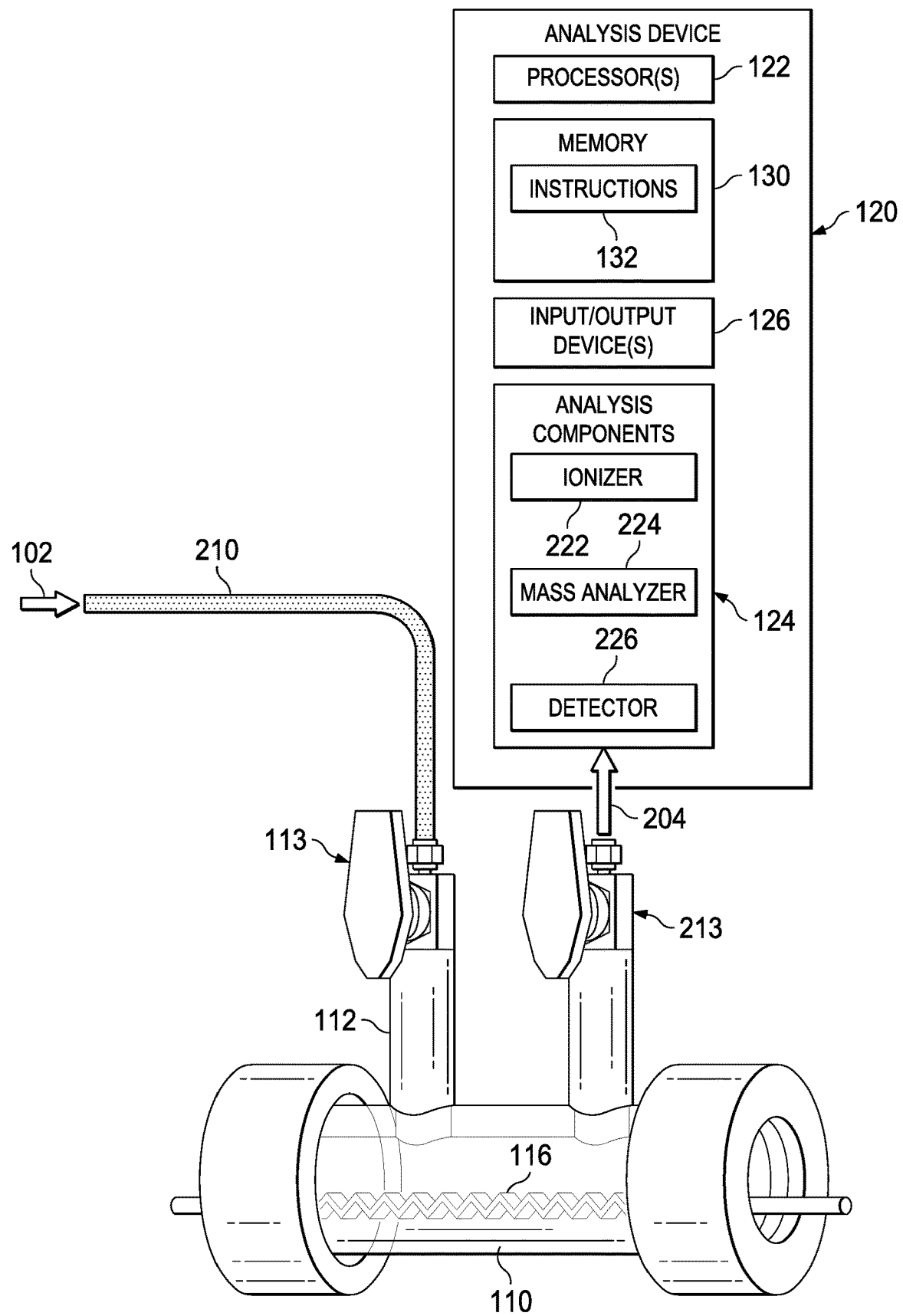
FIG. 2A illustrates a diagram of a mass spectrometer-based system for analyzing breath samples in accordance with aspects of the present disclosure.

Referring to FIG. 2A, exemplary aspects of a system 100A or 100B utilizing mass spectrometer-based analysis components are illustrated. It is noted that in FIGS. 1A through 2B, like reference numbers are utilized to refer to similar components. As shown in FIG. 2A, the analysis components 124 may include an ionizer 222, a mass analyzer 224, and a detector 226. As described above, a breath sample 102 may be provided to the inlet 112 via a mouthpiece 210 when the valve 113 is in an open state. Subsequent to the breath sample 102 being provided to the volume of the sampling chamber 110, the heating mechanism 118 (not shown in FIG. 2A) may be activated, causing resorption of the VOCs adhered to the molecule collector 116. An outlet 204 may be utilized to provide the released VOCs to the analysis components 124. A valve 213 may be configurable to a first state (e.g., an open state) and a second state (e.g., a closed state) to control the providing of the VOCs to the analysis components. For example, in the first state, the VOCs may be allowed to pass through the outlet 204 to the analysis components 124 and in the second state, the VOCs may be prevented from passing through the outlet 204 to the analysis components 124. The ionizer 222 may be configured to ionize at least the portion of the VOCs released from the molecule collector to produce one or more ionized fragments. The mass analyzer 224 may be configured to separate the one or more ionized fragments (e.g., according to a mass-to-charge ratio of the one or more ionized fragments) and the detector 226 may be configured to identify the one or more target VOCs based on the separated one or more ionized fragments. In an aspect, the mass spectrometer components (e.g., the ionizer 222, the mass analyzer 224, and the detector 226) may operate under control of, or in coordination with, a computing device, such as a computing device that includes the one or more processors 122, the memory 130, and the one or more I/O devices 126. For example, the computing device may receive information from the mass spectrometer components, such as information associated with the one or more target VOCs identified in the breath sample 102, and may generate the output representative of the one or more target VOCs based on information associated with the one or more target VOCs. Additionally, the computing device may be configured to display the output at an output device, such as a display device.

In mass spectrometer-based embodiments where the heating mechanism ramps the heat of the sampling chamber the mass spectrometer ionizer may ionize at least the portion of the VOCs released from the molecule collector to produce one or more ionized fragments by first ionizing one or more lighter and/or less bound VOCs released first and later ionizing one or more heavier and/or more strongly bound VOCs released later from the molecule collector by ramping heat, and/or heat of the breath sample within the sampling chamber by the heating mechanism. Likewise, the mass spectrometer mass analyzer may, in such embodiments separate the one or more ionized fragments by first separating one or more ionized fragments of the one or more lighter and/or less bound VOCs released first and later separating one or more ionized fragments of the one or more heavier and/or more strongly bound VOCs. Then, the detector of the mass spectrometer may identify the one or more target VOCs based on the separated one or more ionized fragments, by first identifying one or more lighter and/or less bound target VOCs released first and later identifying one or more heavier and/or more strongly bound target VOCs released later. Also, in such embodiments, the output device may first display information associated with the one or more lighter and/or less bound target VOCs, and later display information associated with the one or more heavier and/or more strongly bound target VOCs.

In embodiments where heating mechanism 118 is a laser configured to ablate VOCs off of the molecule collector (Carboxen mesh), the laser may ablate lighter and/or less bound VOCs first and then ablate heavier and/or more strongly bound (relative to the less bound) VOCs later (last), by varying tuning of the laser's frequency and/or intensity. Whereas, in embodiments where heating mechanism 118 is a photodiode array configured to excite and/or heat the molecule collector to release least a portion of the VOCs from the molecule collector the photodiode array may excite and/or heat the molecule collector, across a (visible and/or invisible light) spectrum and/or over time, to stage release of VOCs off of the molecule collector, with lighter and/or less bound VOCs released first and then heavier and/or more strongly bound (relative to the less bound) VOCs released later (last). In either such case (or where the heating mechanism is an electrically ramped heating elements, analysis device 120 may first identify one or more lighter and/or less bound target VOCs released off of the molecular collector and later identify one or more heavier and/or more strongly bound target VOCs released off of the molecular collector later (last).

Figure 2B:
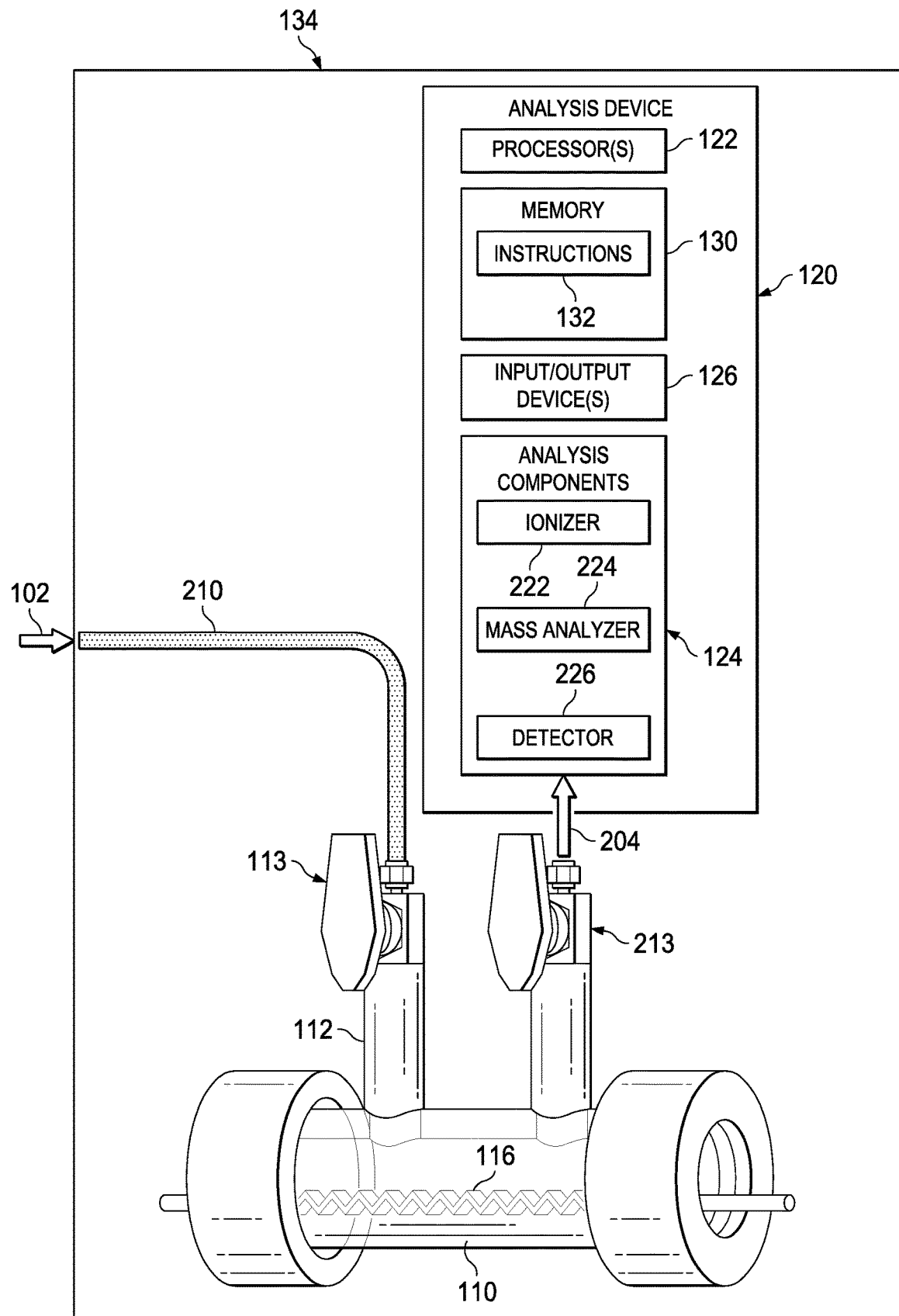
FIG. 2B is a diagram of a mass spectrometer-based system for analyzing breath samples, deployed in a single portable case, or the like, in accordance with aspects of the present disclosure.

As noted above, embodiments of the present system for analyzing breath samples in accordance with aspects of the present disclosure may be housed with a single housing, such as a hard case, or similar protective utility case. FIG. 2B is a diagram of a mass spectrometer-based system for analyzing breath samples, deployed in single portable case 134, or the like, in accordance with aspects of the present disclosure. As noted, housing 134 may be a hard case or similar protective utility case, with (a) carry handle(s), weatherproof seals between a body and lid of the case, and/or the like, and may be primarily made from metal (such as aluminum) or from a durable material such as polypropylene. In such embodiments, a mass spectrometer, such as a mini-mass spectrometer, a computing device communicatively coupled to the mass spectrometer, and an output device communicatively coupled to the computing device are disposed within portable housing 134. For example, analysis components 124 such as ionizer 222, mass analyzer 224 and detector 226 of the (mini) mass spectrometer are operably disposed within portable housing 134.

System 100A or 100B for rapid analysis of a breath sample may also employ a vacuum pump (in housing 134), which may be part of, or deployed in conjunction with the mass spectrometer, to introduce a vacuum in ionizer 222, mass analyzer 224 and detector 226 of the mass spectrometer, such as concurrent with heating of sampling chamber 110 and to draw at least a portion of the VOCs released from the molecule collector by the heating of the sampling chamber into the mass spectrometer. As one of skill in the art will appreciate, spectrometers typically operate at very low pressure (high vacuum). This reduces the chance of ions colliding with other molecules in the mass analyzer. Any collision can cause ions to react, neutralize, scatter, or fragment, which may interfere with the spectrum analysis. To minimize collisions, analysis is undertaken in accordance with embodiments of the present systems and methods under high vacuum conditions, typically $10^{-2}$ to $10^{-5}$ Pa ($10^{-4}$ to $10^{-7}$ torr). This high vacuum may require two pumping stages. The first stage may employ a mechanical pump, or the like, that provides rough vacuum down to 0.1 Pa ($10^{-3}$ torr). The second stage may use a turbomolecular pump, or the like, to provide high vacuum. The (mechanical) vacuum pump(s) may also, subsequent to drawing at least a portion of the VOCs released from the molecule collector into the mass spectrometer, concurrent with generating output representative of the target VOC(s), or before, establish a baseline in system 100A or 100B support cleaning of sampling chamber 110. This establishment of a baseline in system 100A or 100B by cleaning sampling chamber 110 may include further heating the sampling chamber, and, or at least, evacuating the sampling chamber and the mass spectrometer using vacuum provided by the vacuum pump. Establishment of the baseline by clean the sampling chamber by further heating the sampling chamber and evacuating the sampling chamber and the mass spectrometer, using vacuum provided by the vacuum pump(s), may take place, or at least begin, at least in part, earlier, concurrent with at least a portion of identifying target VOC(s), in some embodiments.

Figure 3A:
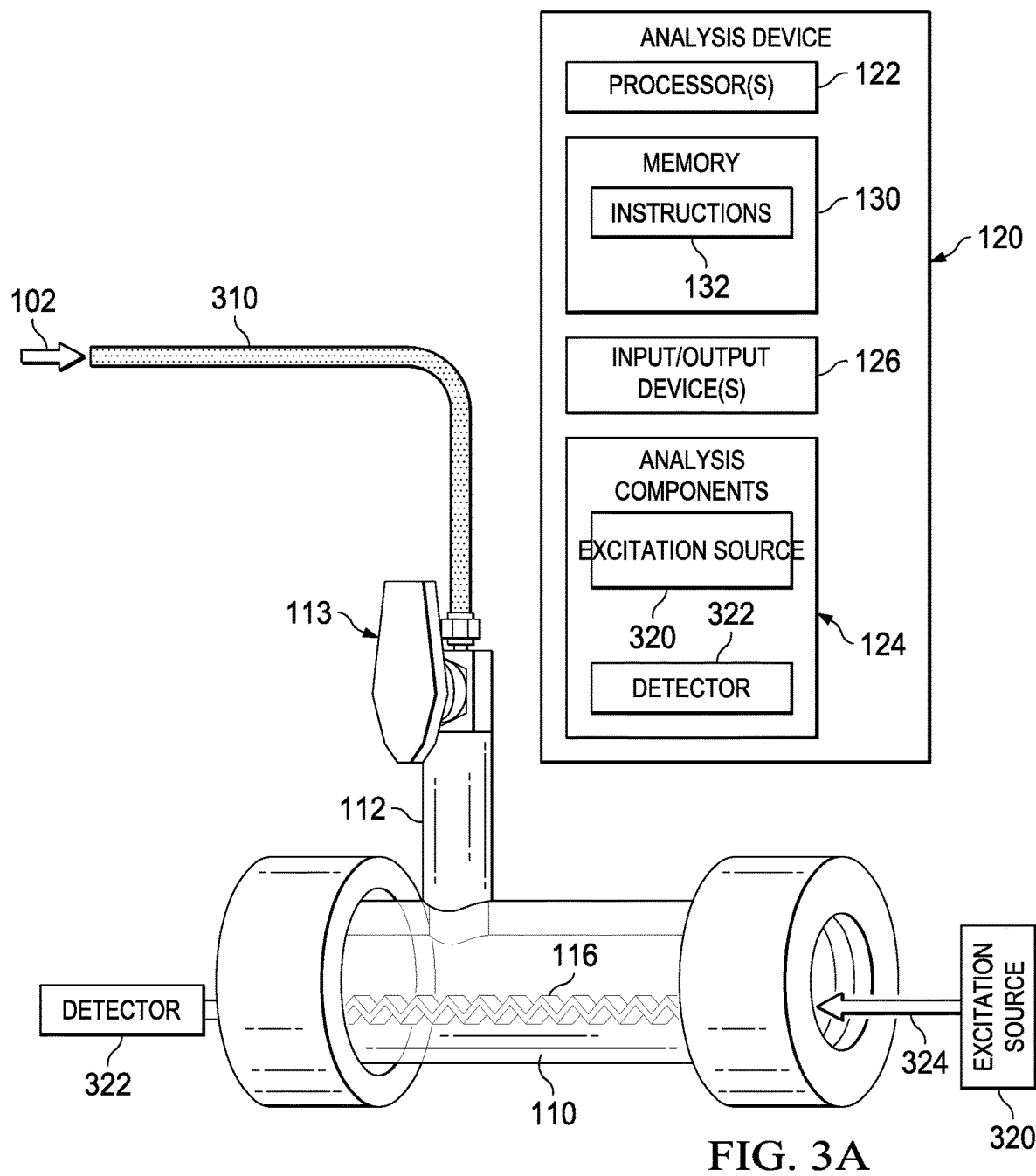
FIG. 3A illustrates a diagram of a Terahertz spectrometer-based system for analyzing breath samples in accordance with aspects of the present disclosure.

Referring to FIG. 3A, exemplary aspects of a system 100A or 100B utilizing THz spectrometer-based analysis components is illustrated. It is noted that in FIGS. 1A through 3B, like reference numbers are utilized to refer to similar components. As shown in FIGS. 2A and 2B, the analysis components 124 may include an excitation source 320 and a detector 322. As described above, a breath sample 102 may be provided to the inlet 112 via a mouthpiece 310 when the valve 113 is in an open state. Subsequent to the breath sample 102 being provided to the volume of the sampling chamber 110, the heating mechanism 118 (not shown in FIG. 3A) may be activated, causing resorption of the VOCs adhered to the molecule collector 116. The excitation source 320 may be configured to introduce an excitation signal 324 within the sampling chamber subsequent to the release of at least a portion of the VOCs from the molecule collector 116 and the detector 322 may be configured to identify the one or more target VOCs based on one or more characteristics associated with excitation of at least the portion of the VOCs released from the molecule collector 116 in response to the excitation signal 324. In an aspect, the excitation source 320 may be a THz laser device and the excitation signal 324 may be a THz laser signal. In aspects, the one or more characteristics associated with the excitation of at least the portion of the VOCs may include at least one of an absorbance characteristic and a fluorescent emission characteristic, which may be utilized to identify the one or more target VOCs present within the breath sample 102, as described in more detail below. In an aspect, the THz spectrometer components (e.g., the excitation source 320 and the detector 322) may operate under control of, or in coordination with, a computing device, such as a computing device that includes the one or more processors 122, the memory 130, and the one or more I/O devices 126. For example, the computing device may receive information from the THz spectrometer components, such as information associated with the one or more target VOCs identified in the breath sample 102, and may generate the output representative of the one or more target VOCs based on information associated with the one or more target VOCs. Additionally, the computing device may be configured to display the output at an output device, such as a display device.

In THz spectrometer-based embodiments where the heating mechanism ramps the heat of the sampling chamber the THz spectrometer the excitation source may introduce an excitation signal within the sampling chamber subsequent to the release of lighter and/or less bound VOCs first and then release of heavier and/or more strongly bound (relative to the less bound) VOCs later (last). The THz spectrometer may then identify the target VOC(s) based on one or more characteristics associated with excitation of at least the portion of the VOCs released from the molecule collector, in response to the excitation signal by first identifying one or more lighter and/or less bound target VOCs released first and later identifying one or more heavier and/or more strongly bound target VOCs released later (last).

Figure 3B:
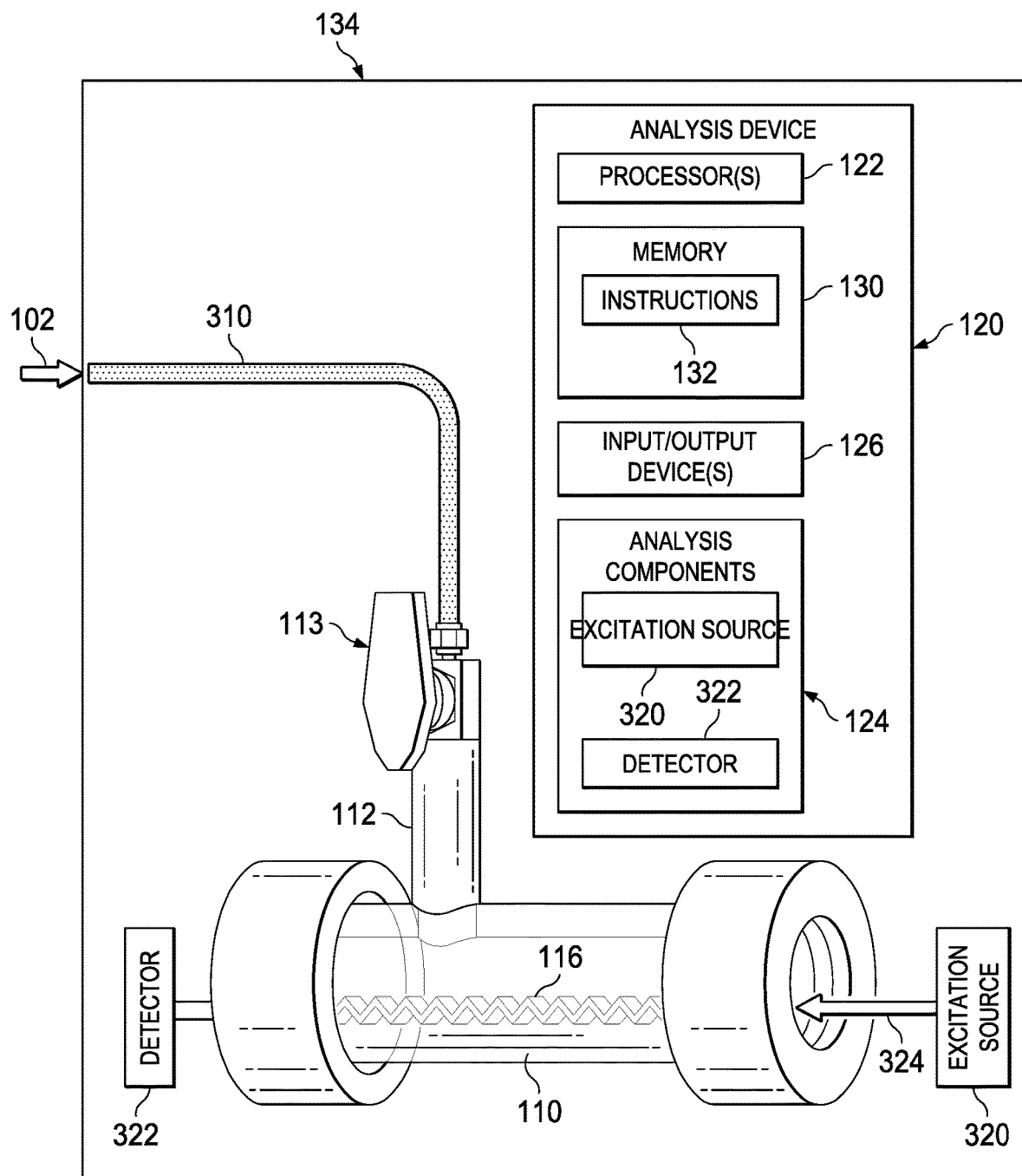
FIG. 3B is a diagram of a Terahertz spectrometer-based system for analyzing breath samples, deployed in a single portable case, or the like, in accordance with aspects of the present disclosure.

As noted above, embodiments of the present system for analyzing breath samples in accordance with aspects of the present disclosure may be housed with a single housing, such as a hard case, or similar protective utility case. FIG. 3B is a diagram of a THz spectrometer-based system for analyzing breath samples, deployed in single portable case 134, or the like, in accordance with aspects of the present disclosure. As noted, housing 134 may be a hard case or similar protective utility case, with (a) carry handle(s), weatherproof seals between a body and lid of the case, and/or the like, and may be primarily made from metal (such as aluminum) or from a durable material such as polypropylene. In such embodiments, a THz spectrometer is disposed within portable housing 134. For example, analysis components 124 such as excitation source 320, such as a THz laser, and detector 322 of the THz spectrometer are operably disposed within portable housing 134.

System 100A or 100B for rapid analysis of a breath sample may also employ a vacuum pump (in housing 134), which may be part of, or deployed in conjunction with the Terahertz (THz) spectrometer which may introduce a vacuum in the detector of the THz spectrometer concurrent with heating of the sampling chamber and draw at least a portion of the VOCs released from the molecule collector by the heating of the sampling chamber into the THz spectrometer detector. The vacuum pump may also, subsequent to drawing at least a portion of the VOCs released from the molecule collector into the THz spectrometer, and at least concurrent with generating output representative of the target VOC(s), establish a baseline in system 100A or 100B by cleaning the sampling chamber by further heating the sampling chamber and evacuating the sampling chamber and the THz spectrometer (detector) using vacuum. Establishment of the baseline by clean the sampling chamber by further heating the sampling chamber and evacuating the sampling chamber (and the THz spectrometer (detector)), using vacuum provided by the vacuum pump, may take place, or at least begin, at least in part, earlier, concurrent with at least a portion of identifying target VOC(s), in some embodiments.

Referring back to FIGS. 1A and 1B, the output representative of the one or more target VOCs may include information that quantitates a concentration of the one or more target VOCs with respect to a source of the breath sample. This information may facilitate a determination of whether a source of the breath sample, such as a person that provided the breath sample 102, is impaired or under the influence of one or more substances (e.g., substances corresponding to the identified one or more target VOCs). By providing information that quantitates the concentration of the one or more target VOCs, more accurate determinations of whether the source is impaired or under the influence of substances may be determined. Additionally, the techniques utilized by the system 100A or 100B (as configured in accordance with FIGS. 2A through 3B) may facilitate more rapid identification and quantitation of the VOC levels, thereby facilitating in field determinations as to whether source is impaired or under the influence of one or more substances, such as THC. For example, unlike existing systems capable of quantitatively analyzing certain VOCs, which take a long time to complete, the system 100A or 100B may facilitate determination and quantization of VOCs in a few seconds, particularly when employing concurrent operation of the vacuum pump(s) and the analysis components of the present systems and methods, thereby facilitating practical use in the field, such as by law enforcement officials.

Figure 4A:
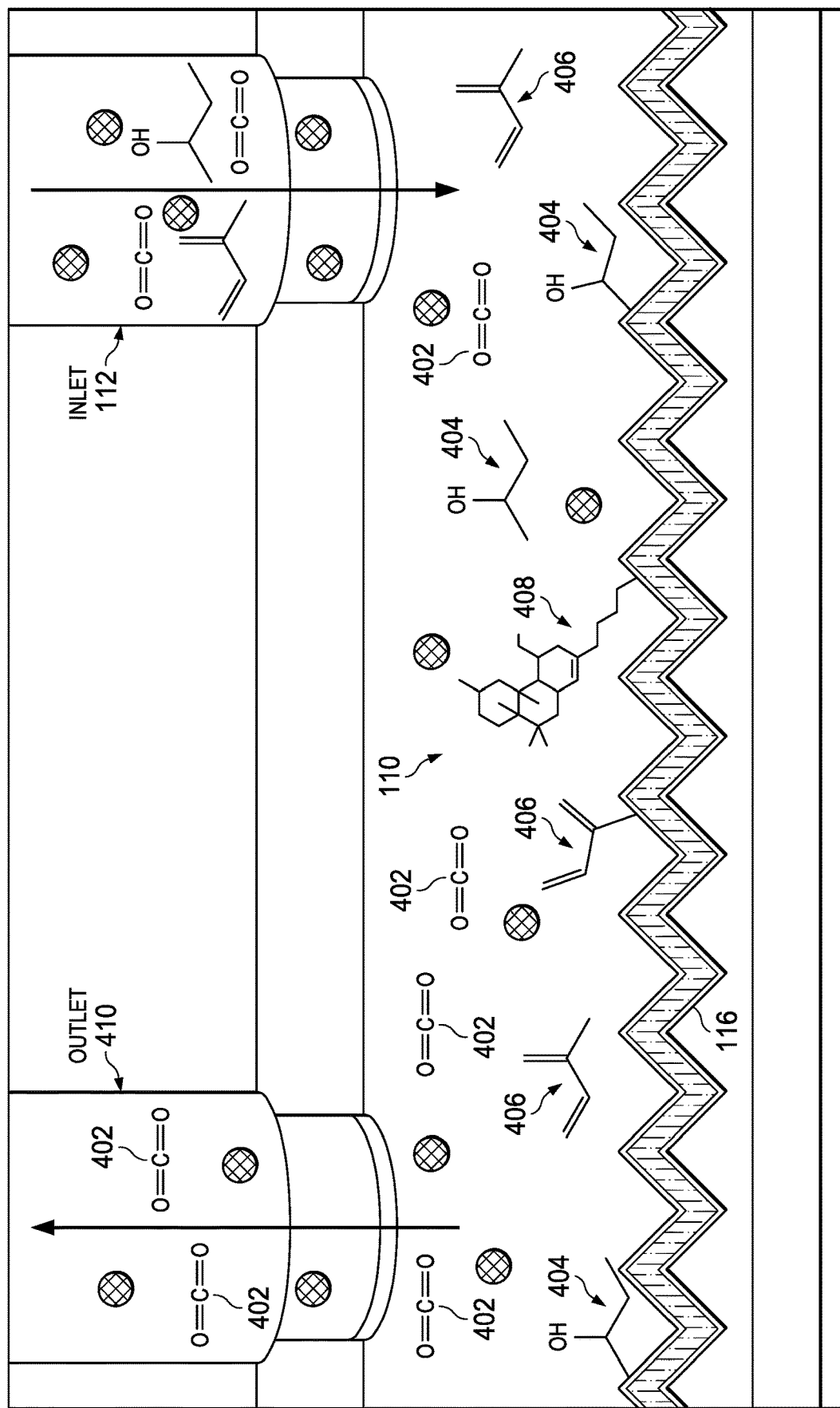
FIG. 4A is a diagram illustrating aspects of receiving a breath sample in a system configured in accordance with aspects of the present disclosure.
Figure 4B:
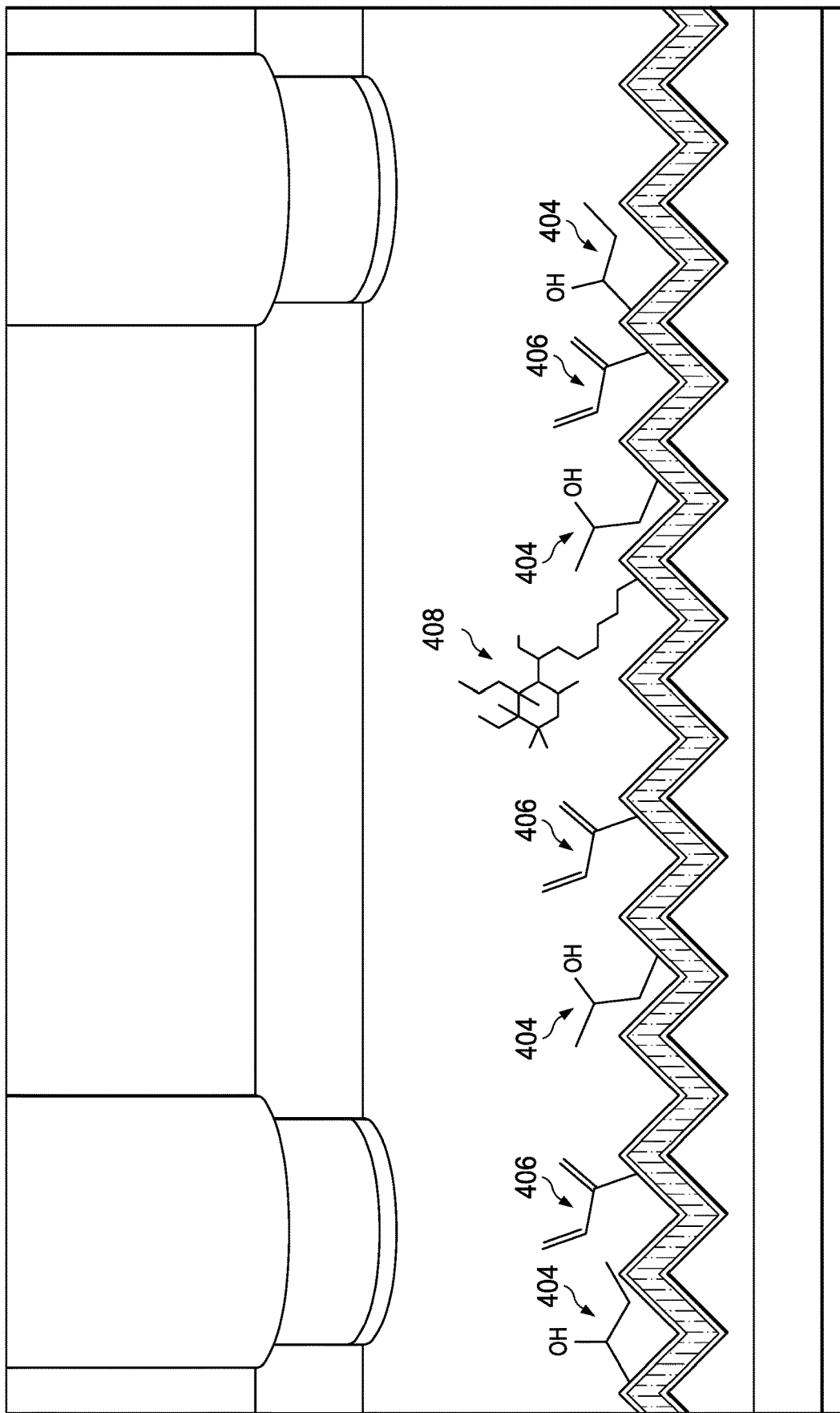
FIG. 4B is a diagram illustrating aspects the behavior of breath sample molecules received in a system configured in accordance with aspects of the present disclosure.
Figure 4C:
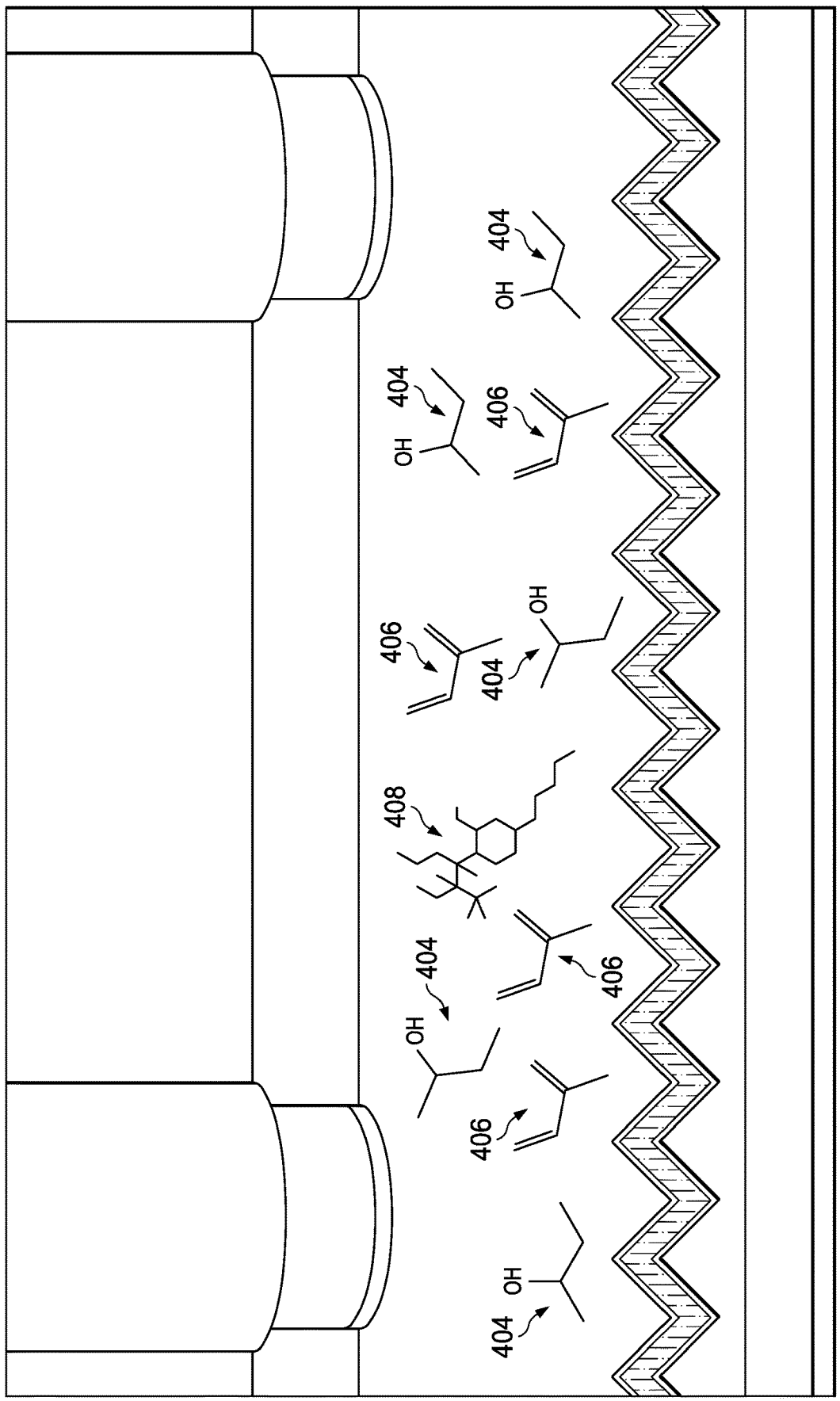
FIG. 4C is a diagram illustrating aspects of analyzing breath sample molecules using a mass spectrometer-based system configured in accordance with aspects of the present disclosure.
Figure 4D:
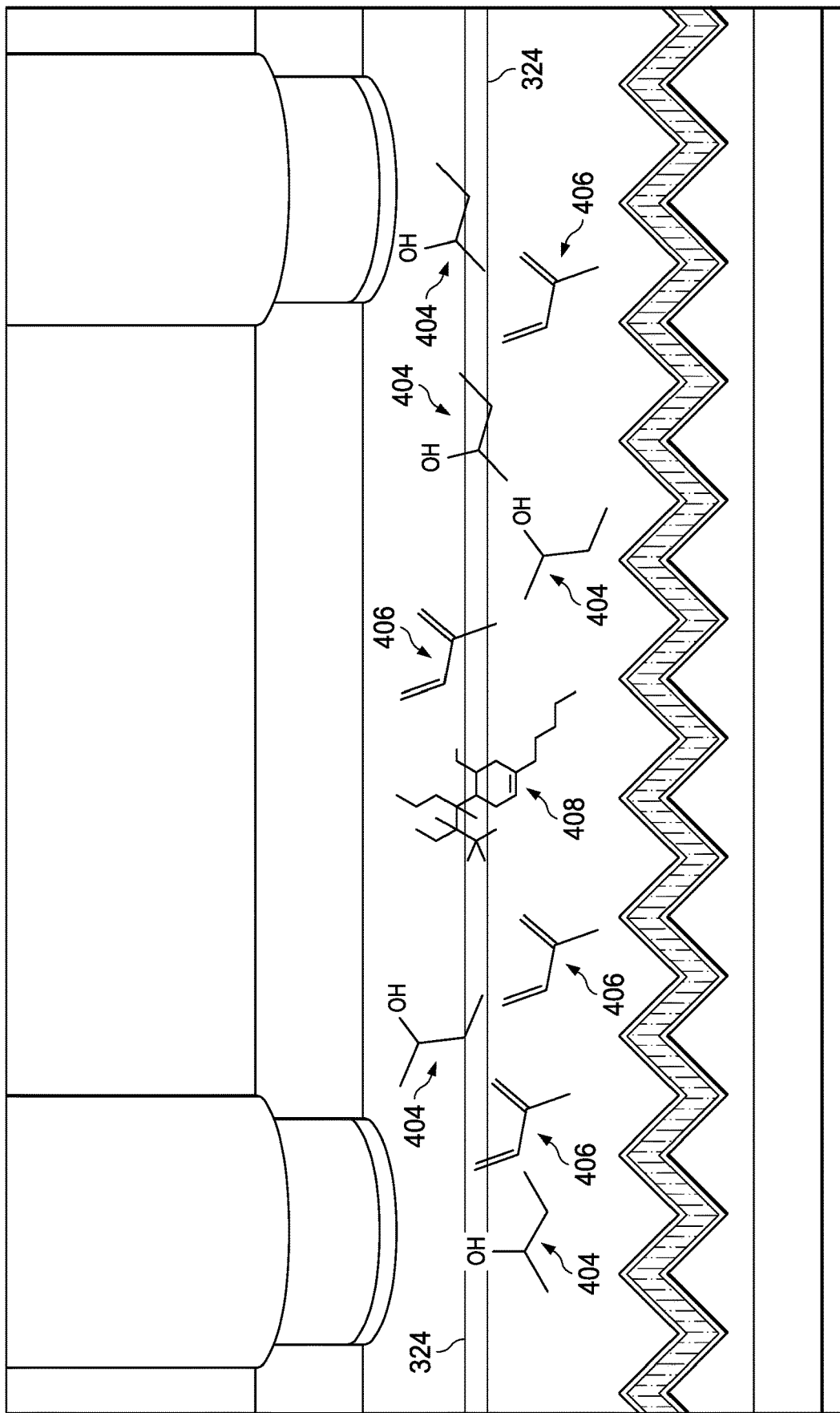
FIG. 4D is a diagram illustrating aspects of analyzing breath sample molecules using a Terahertz (THz) spectrometer-based system configured in accordance with aspects of the present disclosure.

Referring to FIGS. 4A-4D, various aspects of systems for analyzing VOCs present in breath samples in accordance with aspects of the present disclosure are shown. As shown in FIG. 4A, a breath sample may be provided to the sampling chamber 110 via the inlet 112. The breath sample may include one or more VOCs, such as the exemplary VOCs 404, 406, 408 shown in FIG. 4A. Additionally, the breath sample may include non-VOCs, which may include other gases, such as $CO_2$ 402. In an aspect, the sampling chamber 110 may include an outlet 410 configured to release non-VOCs from the sampling chamber 110. It is noted that the outlet 410 is not the same as the outlet 204 of FIGS. 2A and 2B. As shown in FIG. 4B, the VOCs 404, 406, 408 present in the breath sample may adhere to the molecule collector 116. In FIG. 4C, the heating mechanism 118 (not shown in FIGS. 4A-4D) has been activated, introducing heat within the sampling chamber 110, which causes the VOCs to release from the molecule collector 116. After the VOCs are released from the molecule collector 116, the VOCs (or at least a portion of the VOCs) may be provided to a mass spectrometer-based analysis device, such as the analysis device illustrated in FIGS. 2A and 2B, via outlet 204 (not shown in FIG. 4C), for analysis, as described above with reference to FIGS. 2A and 2B. In FIG. 4D, the heating mechanism 118 (not shown in FIGS. 4A-4D) has been activated, introducing heat within the sampling chamber 110, which causes the VOCs to release from the molecule collector 116. After the VOCs are released from the molecule collector 116, the VOCs (or at least a portion of the VOCs) may be provided to a THz spectrometer-based analysis device, such as the analysis device illustrated in FIGS. 3A and 3B, for analysis, as described above with reference to FIGS. 2A and 2B. For example, as illustrated in FIG. 4D, the excitation signal 324 may be provided or projected within the sampling chamber. As described below, excitation of the VOCs by the excitation signal 324 may be utilized by the detector 322 to identify one or more target VOCs present in the breath sample provided to sampling chamber 110.

It is noted that THz spectrometer based systems may provide several advantages over existing systems. For example, using a THz spectrometer may facilitate rapid analysis of breath samples, which may be completed in a matter of seconds, and may facilitate a portable system that can be transported in a local law enforcement vehicle. Additionally, THz spectroscopy-based systems are able to differentiate between Δ-9-THC and CBD because the bonds in the molecules are different. THz spectroscopy or far-infrared spectroscopy may be used to identify compounds that have dipoles that contain a rotational motion. The spectroscopic range is in-between the microwave and infrared region operating at is between 3 mm-30 μm or 0.1-10 THz. Another advantageous aspect of THz spectrometer-based systems is the granularity at which compounds, such as VOCs, may be identified. For example, THz time domain spectroscopy (THz-TDS) is capable of detecting compounds with concentrations as low as parts-per-trillion. THz-TDS works by emitting a pulsed femtosecond laser, which may be a Ti:Sapphire laser. The laser is sent to two photoconductive antennas after being split in a delay line, resulting a probe beam and a pump beam. The pump beams excites a non-linear crystal, which may formed from gallium arsenide (GaAs), and focuses the signal to the sampling space, such as the volume within the sampling chamber 110. The probe beam sends a signal to the second photoconductive antenna, which detects the THz radiation. To obtain a spectrum of a sample a blank must be taken before the sample, which acts as a reference to subtract from the THz spectra of the sample. THz-TDS is useful in determining the torsional deformations of molecules and the intermolecular bonding of molecules. The benefit of analyzing a gas phase compound, such as breath, is that intermolecular bonding interactions are weaker in the gas phase, leaving only the torsional and rotational spectroscopy signal. One challenge faced by THz-TDS for gas analysis is the large presence of water in the atmosphere, which may alter the device's accuracy depending on the altitude of the device. This issue may be overcome by the collection of background before analysis and with the use of a vacuum or a dry inert gas, such as helium, which removes the water in the signal.

The signal of cannabinoids in the breath may be too low for detection via THZ-TDS, however a pre-concentrator may be used to achieve a suitable signal. Previously, pre-concentration devices have been utilized in the analysis of Δ-9-THC using LC/MS. However, those pre-concentration devices utilized sorbent trapping materials which retain water and impair identification of volatile organic compounds (VOCs). To overcome this challenge, the molecule collector 116 described above may utilize carbon molecular sieves, which reduce the amount of water uptake when looking for VOCs. Carbon molecular sieves work by trapping the compound between graphitic planes, allowing molecules to diffuse fast or slow based on the size of the molecule. The molecules can be rapidly emitted when a heating mechanism is applied to the sorbent material as the graphitic planes enlarge. As described above, in the systems of the present disclosure, a conductive material formed from or coated with a carbon molecular sieve sorbent material may be used as the molecule collector. Based on the type of sorbent material, however, the material may release the VOCs at a different rate, allowing a separation to still be achieved. This process of desorption distinguishes certain carbon molecular sieves materials from others in rapid gas analysis techniques. In aspects, the molecule collector 116 may be formed form a VOC desorptive material, such as Carboxen® (e.g., Carboxen® 1000). Carboxen® may be used in rapid VOC gas analysis to identify specific molecules based on emission time. Larger molecules may not be emitted from the graphitic plane faster than the smaller molecules, allowing the smaller compounds to desorb and be analyzed faster than the larger molecules.

In the description that follows, a THz spectroscopy-based system for cannabinoid detection similar to the system described above with reference to FIGS. 3A and 3B, was cross-referenced with a Thermo Fischer PolarisQ mass spectrometer-based system similar to the system described above with reference to FIGS. 2A and 2B. In the experimental setup, a sampling chamber containing a molecule collector formed from a Carboxen® 1000 coated mesh was coupled to a heating mechanism (e.g., a 24-volt power supply). With a valve connecting an inlet and replaceable mouthpiece to the sampling chamber open, a person would exhale a breath into the sampling chamber, trapping the VOCs on the Carboxen® molecule collector. Other VOCs also adhered to the molecule collector, while non-VOC gases flowed over and out of the sampling tube (FIG. 4A). After completion of the exhale, the valve was closed to prevent any extraneous compounds from depositing onto the molecule collector (FIG. 4B). The molecule collector was then supplied with 24 volts to evenly heat the molecule collector and promote rapid desorption of the compounds adhered thereto. For mass spectrometry reference characterization, the released compounds were provided to the mass spectrometer for a signal to be detected (FIG. 4C). Being formed from Carboxen®, the molecule collector also facilitated a separation technique, where smaller VOCs were emitted faster than larger compounds. This enabled a determination of the proper time at which the cannabinoids were emitted from the molecule collector. Once the proper time was determined, the THz spectrometer was used to determine the presence of cannabinoids without the presence of other background signals, aiding in an accurate and precise measurement. Once this time reference of cannabinoids was collected, the sampling chamber was placed in the THz spectrometer-based analysis device, allowing the excitation signal (e.g., a THz laser signal) to be used to detect the samples emitted by the molecule collector (FIG. 4D). The THz spectrometer-based system may act in two manners. The first being that the compounds (e.g., the VOCs) may be emitted from the molecule collector and then be excited via the excitation signal. The excited molecule(s) may then be detected as an absorbance by the detector as it returns to ground state. The other mechanism would be that excitation of the molecule(s) due to the rapid heating of the molecule collector may result in a fluorescent signal being emitted. The system may be configured to determine the presence of cannabinoids and/or other VOCs in the breath sample based on the fluorescent signal emitted in response to the excitation of the VOCs by the excitation signal.

Figure 5:
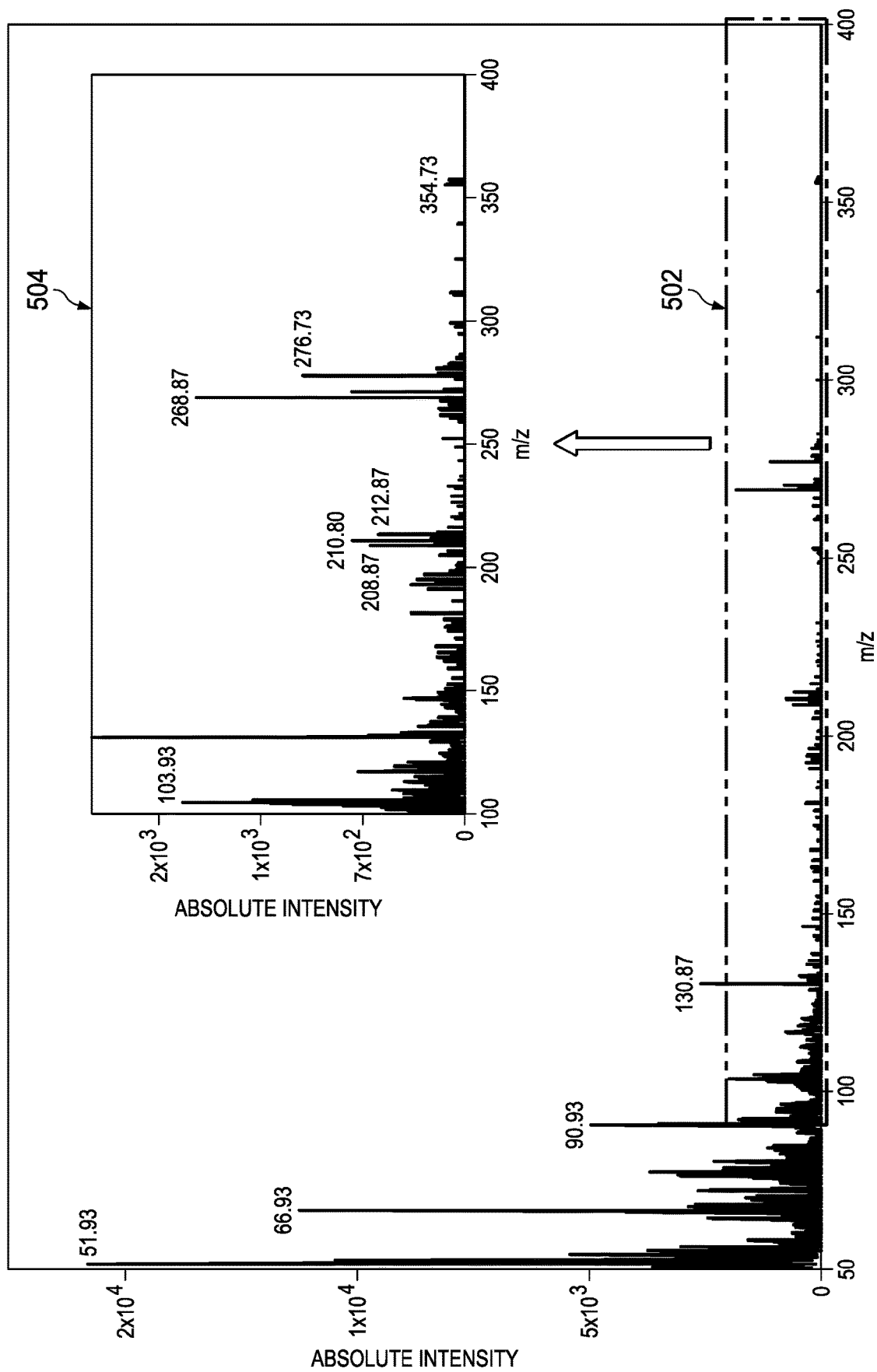
FIG. 5 is a graph illustrating observed VOCs for a healthy breath sample.
Figure 6:
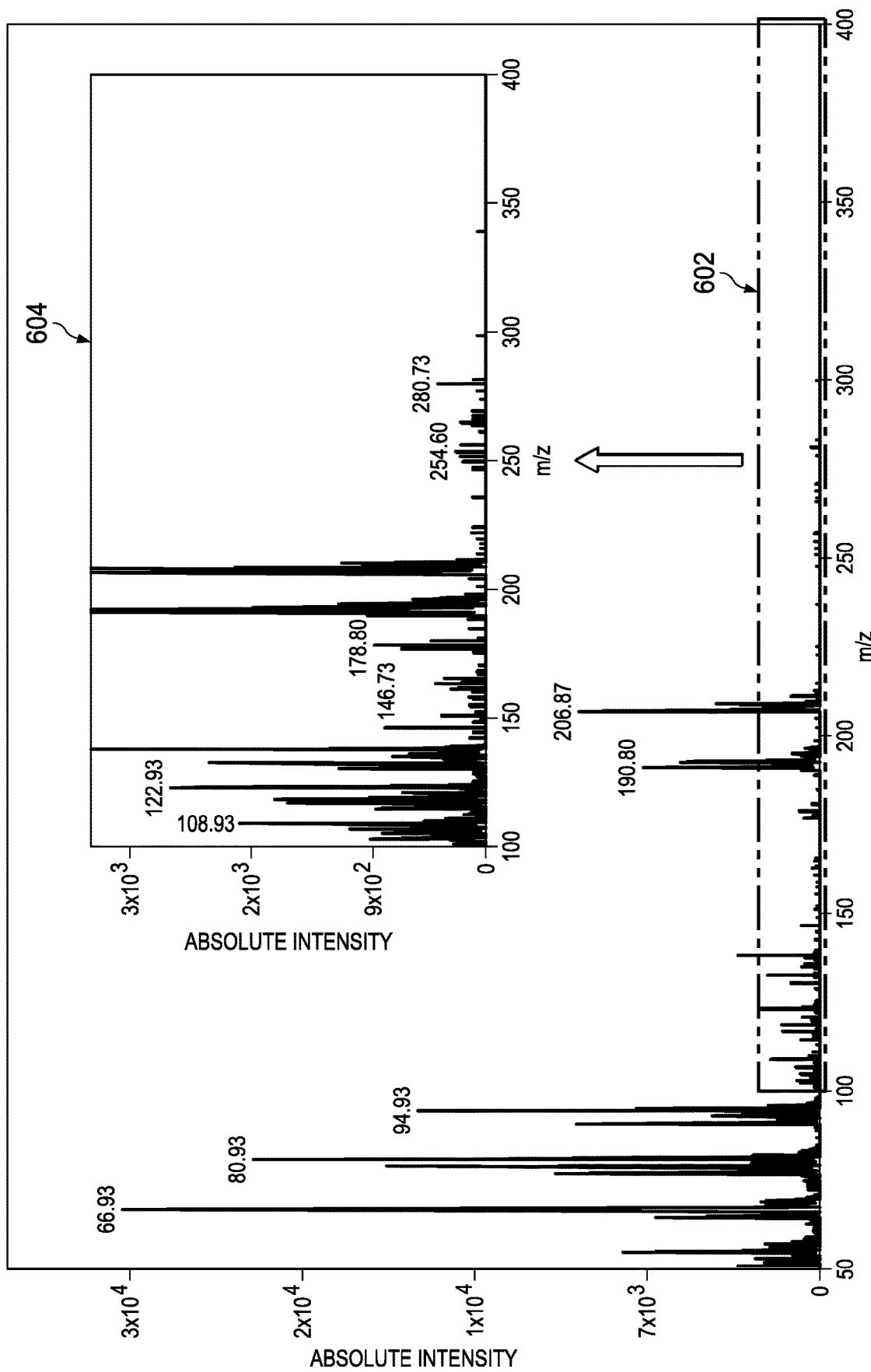
FIG. 6 is a graph illustrating observed VOCs for a breath sample of a person suffering from seasonal allergies.
Figure 7:
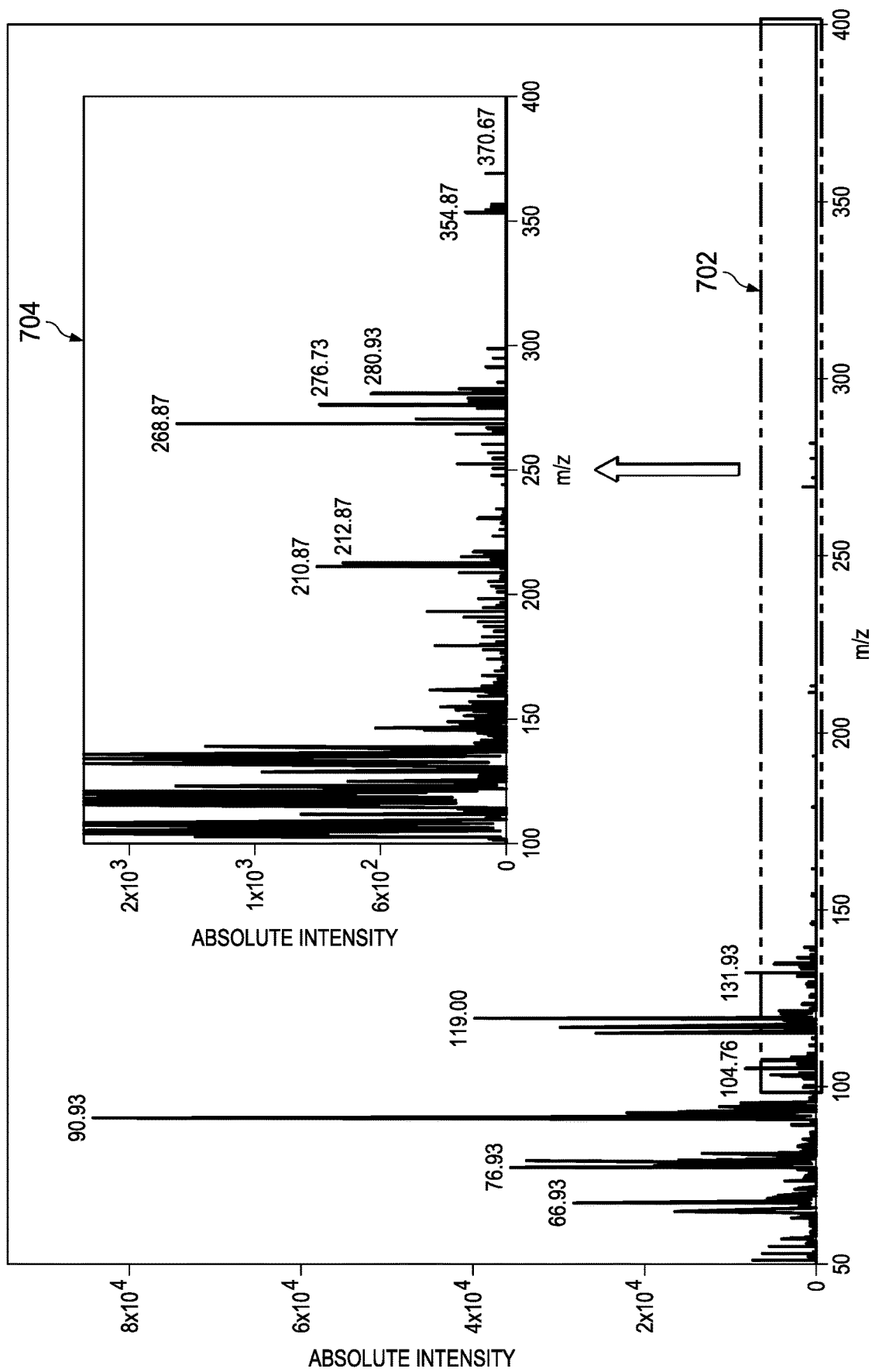
FIG. 7 is a graph illustrating observed VOCs for a breath sample of a person after using mouthwash.

A mass spectrometer-based system was developed and utilized to analyze breath samples. Using this system, differences in the physical state of a person exhaling have already been demonstrated. Healthy breath samples, breath samples from a person suffering from seasonal allergies (allergy breath), and breath samples obtained from a person directly after washing their mouth out with Listerine were collected in sampling chambers having a molecule collector formed from a Carboxen® coated mesh attached to a PolarisQ ion trap mass spectrometer. The results of the analysis performed on each of the breath samples are illustrated in FIG. 5 (healthy breath sample), FIG. 6 (breath sample of a person suffering from seasonal allergies), and FIG. 7 (breath sample from a person directly after washing with Listerine). In FIG. 5, cutout 504 illustrates an enlarged view of the peaks illustrated in box 502. In FIG. 6, cutout 604 illustrates an enlarged view of the peaks illustrated in box 602. In FIG. 7, cutout 704 illustrates an enlarged view of the peaks illustrated in box 702. As shown in FIG. 5, a large 51.93 m/z value was observed, which corresponds to 1-buten-3-yne. This 1-buten-3-yne was not found in the allergy breath sample. In the allergy breath sample, the largest peak was observed at 66.93 m/z, which corresponds to isoprene, followed by peaks at 80.93 m/s (1-methyl-pyrrole) and 94.93 m/z (2-ethylpyrrole), as shown in FIG. 6. In the mouthwash sample, illustrated in FIG. 7, the peak associated with isoprene was lowered, as expected, and other peaks were established, such as the ethylmethylsulfide peak at 76.93 m/z and 1,2,3-propanetriol at 90.93 m/z. Furthermore, larger molecular weight compounds became present, such as the octadecane peak at 254.60 m/z, illustrated in cutout 604. The samples all show a prominent 66.93 m/z peak, which denotes isoprene. Isoprene should be found in all breath samples and may be used as a reference to ensure that the instrument is sampling the breath VOCs. As shown in FIGS. 5-7, prominent changes in the observed compounds were found in the three different scenarios presented. Utilizing this instrument as a reference, determination of cannabinoids in breath samples was achieved using the terahertz spectrometer, as described below.

Figure 8:
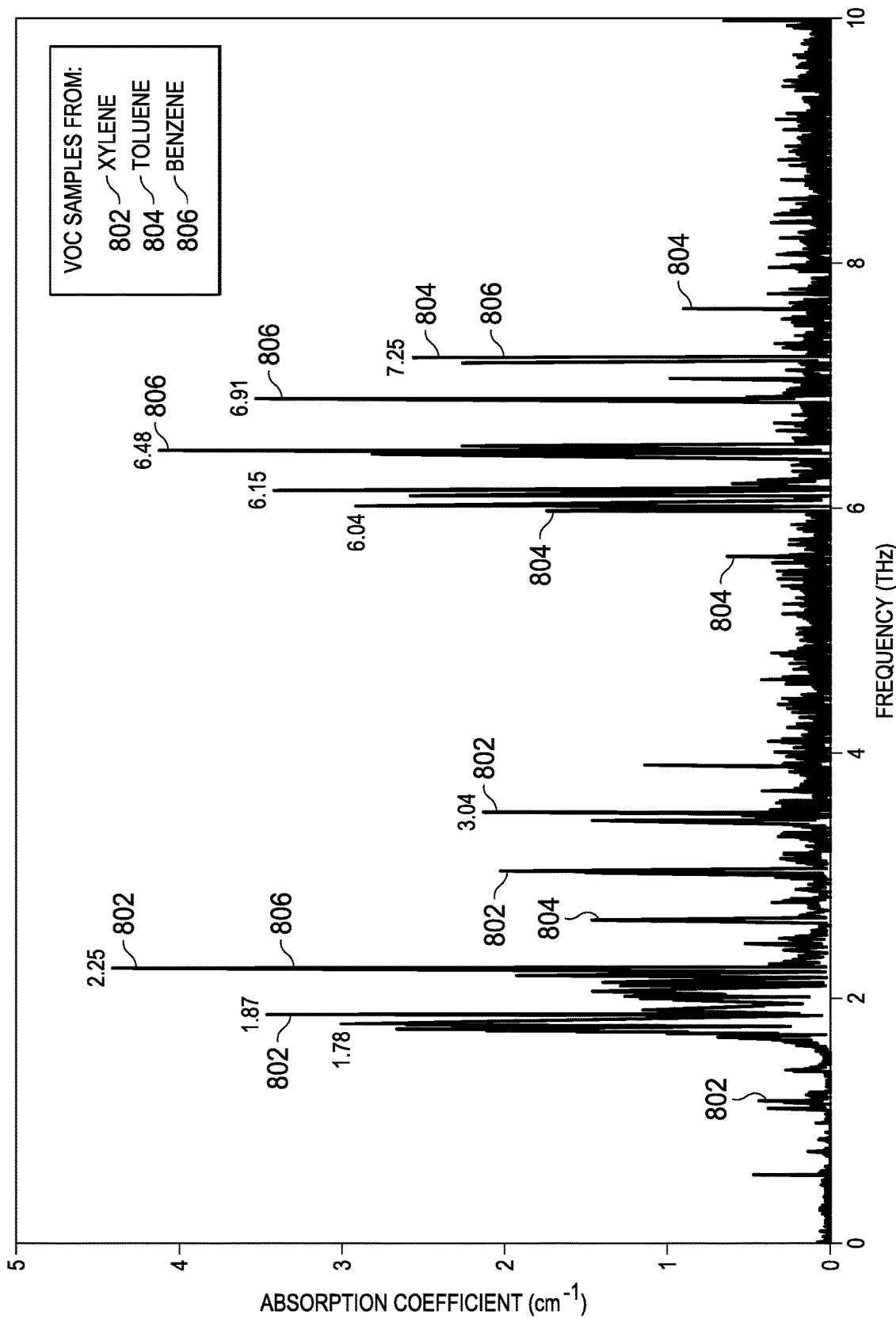
FIG. 8 is a graph illustrating observed VOCs for toluene, benzene, and xylene.
Figure 9:
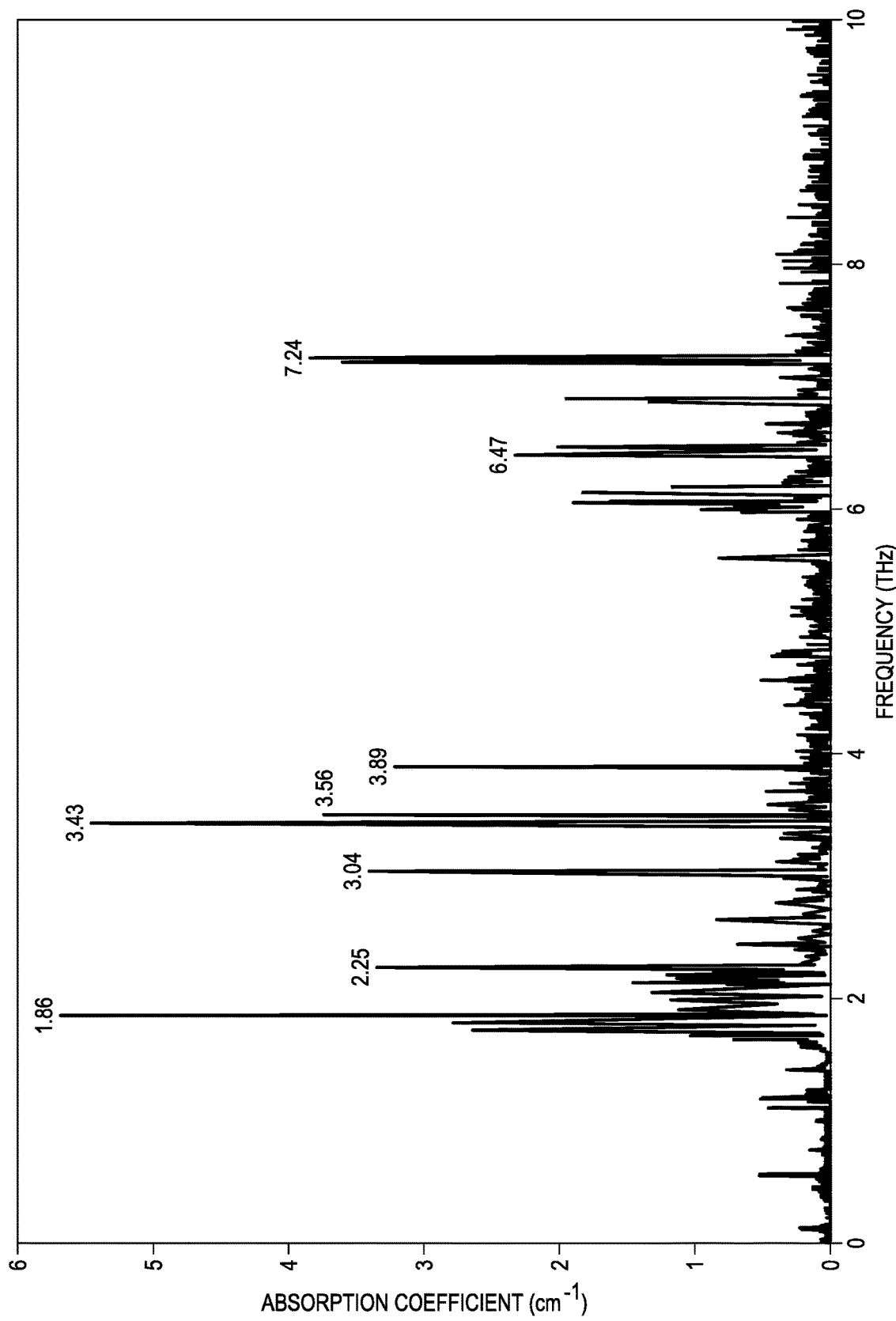
FIG. 9 is a graph illustrating observed VOCs for a marijuana sample.

The terahertz spectra of benzene, toluene, and xylene were acquired and compared to the terahertz spectra of a gas sample of heated marijuana leaves using a MenloSystems (Martinsried, Germany) K15 Time Domain Terahertz Spectrometer. This instrument was used to pump a dry gas, Helium, into a flask, forcing the volatile vapors out and into the sampling chamber where the VOCs adhered to a Carboxen®-based molecule collector. A voltage was then applied to the molecule collector, releasing the VOCs. The results observed for benzene, toluene, and xylene are illustrated in FIG. 8, where lines 802 represent VOCs resulting from xylene, lines 804 represent VOCs resulting from toluene, and lines 806 represent VOCs from benzene. FIG. 9 illustrates VOCs observed from the marijuana sample. The analysis of the gaseous samples allowed the rotational spectroscopy to be obtained, explaining the low signal obtained for benzene at any of the frequencies scanned. The marijuana sample resulted in the most number of rotational bonds, which is to be expected as it was not a pure sample. The xylene and toluene appeared to be the same peak, however the xylene consistently resulted in a lower frequency peak, while the toluene appeared at a higher frequency. This is because xylene has two methyl groups attached to the aromatic ring, while the toluene only has one methyl group attached to the aromatic ring.

Methods to quantitate gas based on terahertz spectra have been done using cigarette smoke using continuous wave terahertz spectroscopy. However, to do so a database to input variables for the Lorentzian fit equation is required. Cannabinoids have not yet been databased, preventing the Lorentzian fit equation from being useful in cannabinoid quantitation. However, quantitation can still be achieved using the absorbance coefficient of the terahertz spectra. Based on the transmission of the sample THz field compared to the transmission field the measured transmission t(f), the absorbance coefficient can be calculated as:

$$n_s(f) = 1 - \frac{c\phi(f)}{2\pi f d} \quad (1)$$

were ns(f) is the sample refractive index, c us the speed of light in a vacuum, ϕ(f) is the phase difference between the transmission of the sample terahertz field and the transmission of the reference terahertz field, f is the frequency, and d is the sample thickness. The sample thickness may be the length of the sampling chamber, which was 9 cm in the above-described examples. The sample refractive index, expressed as:

$$\alpha(f) = -\frac{2}{d}\ln\frac{|t(f)|}{RL} \quad (2)$$

$$RL = \frac{4n_s}{(1+n_s)^2} \quad (3)$$

may be calculated the absorption coefficient α(f) can be calculated, where the loss of signal at the interface is equal to RL. Subtracting the sample spectra from the reference spectra allows the Beer-Lambert law to be used as follows:

$$\alpha(f) = -\frac{\ln T(f)}{d} \quad (4)$$

where T(f) is equal to the ratio between the intensity of the sample transmitted THz field and the reference transmitted THz field. This may allow for a rapid quantitation of Δ-9-THC. A breath sample analyzer system in accordance with the present disclosure may be configured (e.g., via software stored as instructions) to utilize these equations to calculate the concentration of cannabinoids from the breath of the person. The sample volume may change from person to person. Accordingly, the system may be configured to take the overall volume of the breath sample that the person has exhaled into consideration so as to avoid or mitigate inaccuracies in the determined concentration.

Identifying and quantitating, by an analysis device in accordance with embodiments of the present systems and methods, target VOC(s) in the portion of the VOCs released from the molecule collector, may be based, at least in part, on correlation of presence and quantity of the target VOC(s) to a blood level of a substance of interest. Likewise, generation, by the analysis device, of an output representative of the target VOC(s) may include information that quantitates a concentration of the target VOC(s) with respect to a source of the breath sample and the blood level of a substance of interest.

Such blood-to-breath correlations may be derived mathematically or from a National Institute of Standards and Technology (NIST) blood-to-breath table, or the like. Further, in accordance with embodiments of the present systems and methods proprietary blood-to-breath tables may be developed for substances of interest, metabolites (thereof) and metabolite markers (thereof) and used to identify and/or quantitate target VOC(s) in the portion of the VOCs released from the molecule collector, by an analysis device, in the present systems and methods. As noted, the one or more target VOCs may include Δ-9-Tetrahydrocannabinol (Δ-9-THC), THC metabolites, opioids, opioid metabolites, or a combination thereof. Additionally, or alternatively, as noted, the one or more target VOCs may include metabolites, metabolite markers, or a combination thereof indicative of a particular disease and/or identification of a particular disease. For example, ketones and aldehydes (VOC's) that are relatively unique to a particular viral infection (e.g., COVID-19, influenza, rhinovirus, etc.), bacterial infection, or the like. Hence, in accordance with some example embodiments of the present systems and methods, the output may be representative of one or more target VOCs comprising metabolites, metabolite markers, or a combination thereof indicative of such disease(s), such as SARS-CoV-2 and/or Coronavirus Disease 2019 (COVID-19) caused by SARS-CoV-2.

Identifying and quantitating target VOC(s) from among the VOCs present in the sampling chamber may also, or alternatively, include identifying and quantitating one or more target metabolites and/or metabolite markers, and the output representative of the target VOC(s) representative of the target VOC(s) may include information that indicates the presences and/or quantitates a concentration of one or more metabolites and/or metabolite markers. As noted, the one or more target VOCs may include Δ-9-Tetrahydrocannabinol (Δ-9-THC), THC metabolites, opioids, opioid metabolites, or a combination thereof. Thus, the output may include information that indicates the presences and/or quantitates a concentration of one or more metabolites and/or metabolite markers to establish prior use of the substance of interest, and may establish a time frame of such prior use of the substance of interest. Additionally, or alternatively, as noted, the one or more target VOCs may include metabolites, metabolite markers, or a combination thereof indicative of a particular disease and/or identification of a particular disease. For example, ketones and aldehydes (VOC's) that are relatively unique to a particular viral infection (e.g., COVID-19, influenza, rhinovirus, etc.), bacterial infection, or the like. Hence, in accordance with some example embodiments of the present systems and methods, the output may quantitate a severity of the particular disease based at least in part on a type and/or concentration of the metabolites, metabolite markers, or a combination thereof.

Additionally, a Fourier Transform may be used, such as by a computing device communicatively coupled to, or as a part of, the analysis device, to eliminate background noise to arrive at the correlation of presence and quantity of the target VOC(s) to a blood level of a substance of interest to identify and/or quantitate target VOC(s) from among the VOCs present in the sampling chamber. Additionally, or alternatively, a Fourier Transform may be used to eliminate background noise to generate the output representative of the VOC(s) quantitating a concentration of the target VOC(s) with respect to a source of the breath sample and the blood level of the substance of interest.

Figure 10:
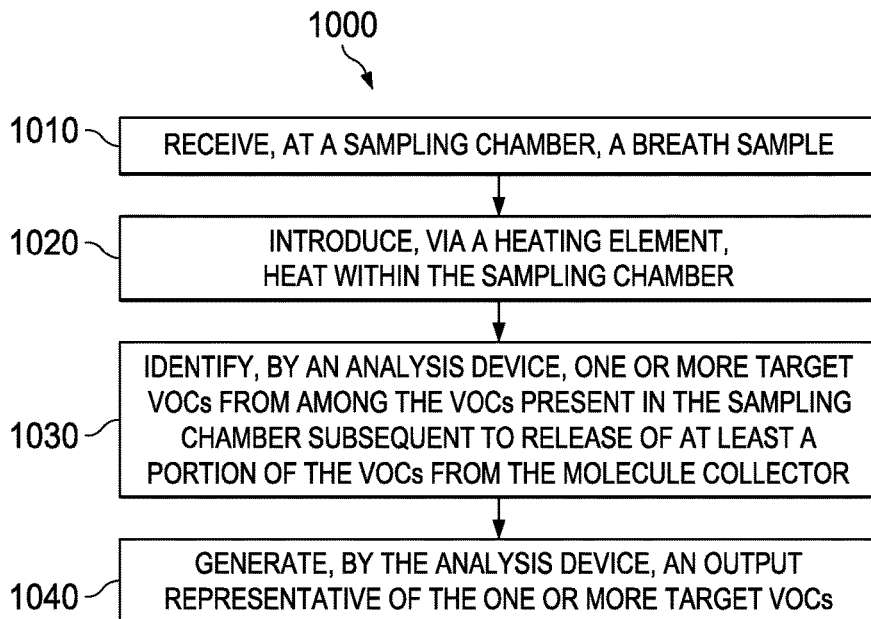
FIG. 10 is a flow diagram of a method for analyzing a breath sample in accordance with aspects of the present disclosure.

Referring to FIG. 10, a flow diagram of a method for analyzing a breath sample in accordance with aspects of the present disclosure is shown as a method 1000. In an aspect, the method 1000 may be performed by the system 100A and 100B of FIGS. 1A and 1B, which may utilize a mass spectrometer-based approach, as described above with reference to FIGS. 2A and 2B or a THz spectrometer-based approach, as described above with reference to FIGS. 3A and 3B. In an aspect, operations or steps of the method 1000 may be realized as a program or instructions (e.g., the instructions 132 of FIGS. 1A-3B) stored at a memory (e.g., the memory 130 of FIGS. 1A-3B) that, when executed by one or more processors (e.g., the one or more processors 122 of FIG. 1A-3B), cause the one or more processors to perform operations for analyzing a breath sample in accordance with aspects of the present disclosure.

As shown in FIG. 10, the method 1000 includes, at step 1010, receiving, at a sampling chamber, a breath sample. As described above, the breath sample may be received at the sampling chamber via an inlet (e.g., the inlet 112 of FIGS. 1A and 1B) coupled to the sampling chamber (e.g., the sampling chamber 110 of FIGS. 1A and 1B) and the sampling chamber may include a molecule collector (e.g., the molecule collector 116 of FIGS. 1A and 1B) disposed within the sampling chamber. At step 1020, the method 1000 includes introducing, via a heating mechanism, heat within the sampling chamber. In an aspect, the heat may be introduced by the heating mechanism 118 of FIGS. 1A and 1B. At step 1030, the method 1000 includes identifying, by an analysis device, one or more target VOCs from among the VOCs present in the sampling chamber subsequent to release of at least a portion of the VOCs from the molecule collector. As described above, at least the portion of the VOCs may be released from the molecule collector by the heat introduced within the sampling chamber by the heating mechanism (e.g., at step 1020). The analysis device may be a mass spectrometer-based device, as described above with reference to FIGS. 2A and 2B, or may be a THz spectrometer-based device, as described above with reference to FIGS. 3A and 3B. At step 1040, the method 1000 includes generating, by the analysis device, an output representative of the one or more target VOCs. In an aspect, the one or more target VOCs may be associated with one or more of Δ-9-THC, 11-hydroxytetrahydrocannabinol (11-OH-THC), carboxy-tetrahydrocannabinol (THC-COOH), THC metabolites, opioids (e.g., methadone and fentanyl, opioid metabolites). Additionally, or alternatively, as noted, the one or more target VOCs may include metabolites, metabolite markers, or a combination thereof indicative of a particular disease and/or identification of a particular disease. For example, ketones and aldehydes (VOC's) that are relatively unique to a particular viral infection (e.g., COVID-19, influenza, rhinovirus, etc.), bacterial infection, or the like. Also, as described above, the output representative of the one or more target VOCs may include information that quantitates a concentration of the one or more target VOCs with respect to a source of the breath sample, such as a person providing the breath sample. Hence, in accordance with some embodiments of the present systems and methods, the output may be representative of one or more target VOCs may indicate the presences and/or quantitate a concentration of one or more metabolites and/or metabolite markers to establish prior use of a substance of interest, may establish a time frame of such prior use of the substance of interest, quantitate a severity of a particular disease, or the like, based at least in part on a type and/or concentration of the metabolites, metabolite markers, or a combination thereof.

Figure 11:
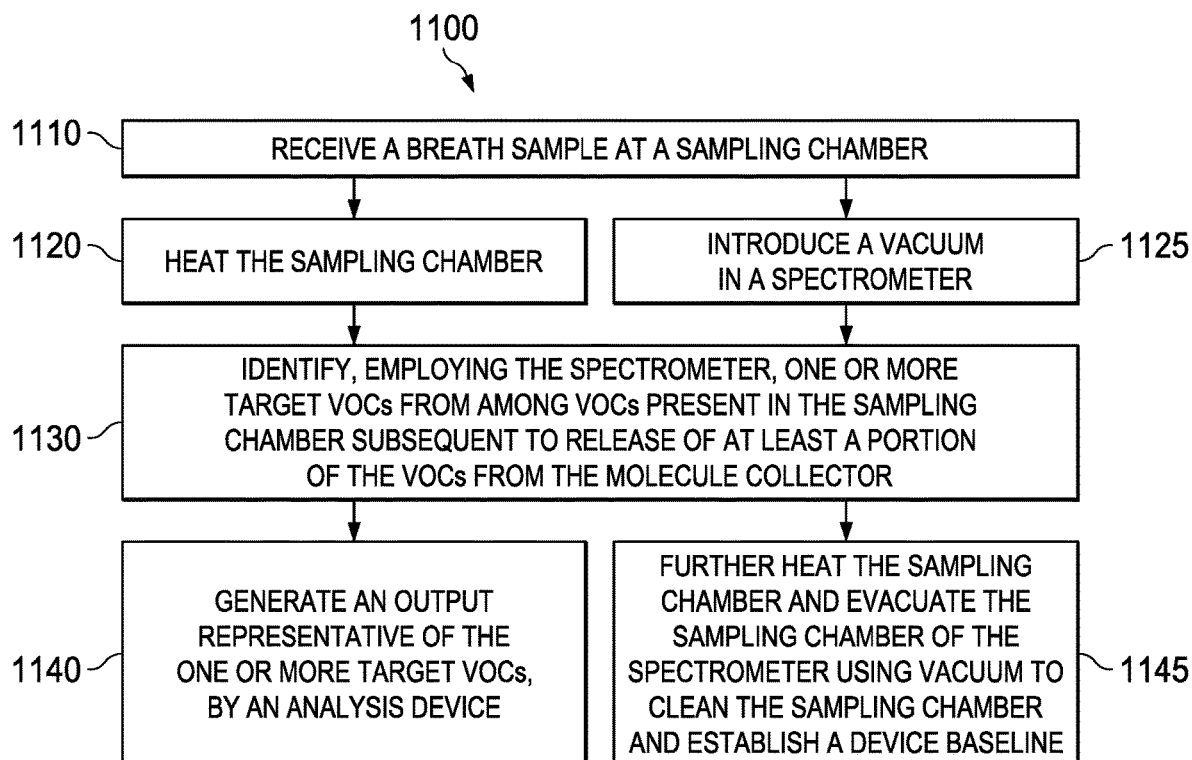
FIG. 11 is a flow diagram of a method for parallel operation of analysis of a breath sample, in accordance with aspects of the present disclosure.

FIG. 11 is a flow diagram of method 1100 for parallel operation of rapid analysis of a breath sample, in accordance with aspects of the present disclosure. Therein, at 1110, a breath sample is received at a sampling chamber, via an inlet coupled to the sampling chamber that includes a molecule collector disposed within the sampling chamber, such that VOCs present in the breath sample adhere to the molecule collector.

At 1120 the sampling chamber is heated and concurrently, at 1125 a vacuum is introduced in a spectrometer. For example, a first vacuum stage may employ a mechanical pump, or the like, to provide rough vacuum down to 0.1 Pa ($10^{-3}$ torr) and a second vacuum stage may use a turbomolecular pump, or the like, to provide high vacuum, $10^{-2}$ to $10^{-5}$ Pa ($10^{-4}$ to $10^{-7}$ torr). At 1130 an analysis device employs the spectrometer to identify one or more target VOCs from among the VOCs present in the sampling chamber subsequent to release of at least a portion of the VOCs from the molecule collector. At least this portion of the VOCs are released from the molecule collector by the heat introduced within the sampling chamber at 1120.

At 1140 the analysis device generates an output representative of the target VOC(s). This output includes information that quantitates a concentration of the target VOC(s) with respect to a source of the breath sample.

Concurrent with generating the output representative of the target VOC(s) at 1140, or before, a baseline for the system is established at 1145 by cleaning the sampling chamber by further heating the sampling chamber and evacuating the sampling chamber of the spectrometer using (the) vacuum. This establishment of the baseline by cleaning the sampling chamber at 1145 may also, at least in part be carried out concurrent with at least a portion of identifying target VOCs at 1130.

As shown above, breath analysis systems and methods in accordance with the present disclosure may provide devices that facilitate detection of cannabinoids and other substances from breath samples in the field. Such systems may be utilized by law enforcement personnel to rapidly and accurately identify/determine whether drivers are DUIM. The ability to make such determinations in the field greatly enhances the capabilities of the criminal justice field with respect to detecting and addressing this issue. For example, previous techniques required a sample to be obtained and then sent to a lab, taking minutes or hours. This long analysis time prevents any action from being properly taken at the scene of the event. In contrast, utilizing breath analysis systems in accordance with the present disclosure, local law enforcement agents can obtain conclusive evidence on scene. This application of the instrument challenges other fields to shift towards furthering the detection of DUIM drivers, removing them from the roads, and enhancing the safety of other drivers. Additionally, the breath analysis systems of the present disclosure may facilitate detection of other illicit drugs with rapid and portable techniques. In addition to detection in the field, the ability to accurately quantitate the concentration of cannabinoids provided by the disclosed systems may provide the ability to develop a standard concentration used to define whether a person is DUIM.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

What is claimed is:

1. A system for analyzing a breath sample, the system comprising:
    a sampling chamber;
    an inlet coupled to the sampling chamber and configured to receive a breath sample and to provide the breath sample to the sampling chamber;
    a molecule collector disposed within the sampling chamber, wherein the molecule collector is configured to adhere volatile organic compounds (VOCs) present in the breath sample;
    a laser configured to ablate VOCs off of the molecule collector;
    an analysis device configured to:
        identify one or more target VOCs from among the VOCs present in the sampling chamber subsequent to ablation of at least a portion of the VOCs from the molecule collector, at least the portion of the VOCs ablated off of the molecule collector by the laser within the sampling chamber; and
        generate an output representative of the one or more target VOCs; and
    a vacuum pump configured to introduce a vacuum in the analysis device, concurrent with ablating VOCs off of the molecule collector, the laser and the vacuum pump also configured to, at least concurrent with generating output representative of the one or more target VOCs, clean the system by the laser further heating the sampling chamber and evacuating the sampling chamber and the analysis device using the vacuum.

2. The system of claim 1, wherein the molecule collector comprises a Carboxen® coated mesh.

3. The system of claim 1, wherein the laser ablates lighter and/or less bound VOCs first and then ablates heavier and/or more strongly bound VOCs later.

4. The system of claim 3, wherein, the laser ablates lighter and/or less bound VOCs first and then ablate heavier and/or more strongly bound VOCs later, by varying tuning of the laser's frequency and/or intensity.

5. The system of claim 3, wherein the analysis device first identifies one or more lighter and/or less bound target VOCs ablated off of the molecule collector first and later identifies one or more heavier and/or more strongly bound target VOCs ablated off of the molecule collector later.

6. The system of claim 1, wherein the analysis device comprises a mass spectrometer, a computing device communicatively coupled to the mass spectrometer, and an output device communicatively coupled to the computing device, and wherein:
    the mass spectrometer includes:
        an ionizer configured to ionize at least the portion of the VOCs ablated from the molecule collector to produce one or more ionized fragments;
        a mass analyzer configured to separate the one or more ionized fragments; and
        a detector configured to identify the one or more target VOCs based on the separated one or more ionized fragments; and
    the computing device includes:
        one or more processors configured to:
            generate the output representative of the one or more target VOCs based on information associated with the one or more target VOCs identified by the detector; and
            display the output at the output device; and
        a memory communicatively coupled to the one or more processors.

7. The system of claim 1, wherein the analysis device comprises a Terahertz (THz) spectrometer that includes:
    an excitation source configured to introduce an excitation signal within the sampling chamber subsequent to the ablation of at least a portion of the VOCs from the molecule collector; and
    a detector configured to identify the one or more target VOCs based on one or more characteristics associated with excitation of at least the portion of the VOCs ablated off of the molecule collector, in response to the excitation signal.

8. The system of claim 7, wherein the excitation source comprises a THz laser.

9. The system of claim 7, wherein the one or more characteristics associated with the excitation of at least the portion of the VOCs comprises at least one of an absorbance characteristic and a fluorescent emission characteristic.

10. The system of claim 1 further comprising a sensor configured to determine whether the breath sample satisfies one or more criterion.

11. The system of claim 1, wherein the one or more target VOCs include:
    metabolites, metabolite markers, ketones, aldehydes, or a combination thereof indicative of SARS-CoV-2 and/or Coronavirus Disease 2019 (COVID-19) caused by SARS-CoV-2; and/or
    Δ-9-THC, 11-hydroxy-tetrahydrocannabinol (11-OH-THC), carboxy-tetrahydrocannabinol (THCCOOH), THC metabolites, opioids, opioid metabolites, or a combination thereof.

12. A method for analyzing a breath sample, the method comprising:
    receiving, at a sampling chamber, a breath sample via an inlet coupled to the sampling chamber, wherein the sampling chamber comprises a molecule collector disposed within the sampling chamber, and wherein the molecule collector is configured to adhere volatile organic compounds (VOCs) present in the breath sample;

ablating, by a laser, VOCs off of the molecule collector;

concurrent with ablating VOCs off of the molecule collector, introducing a vacuum in an analysis device;

identifying, by the analysis device, one or more target VOCs from among the VOCs present in the sampling chamber subsequent to release of at least a portion of the VOCs from the molecule collector, wherein at least the portion of the VOCs are released from the molecule collector by the laser ablating VOCs off of the molecule collector;

generating, by the analysis device, an output representative of the one or more target VOCs, wherein the output representative of the one or more target VOCs comprises information that quantitates a concentration of the one or more target VOCs with respect to a source of the breath sample; and concurrent with at least generating the output representative of the one or more target VOCs, cleaning the sampling chamber by:

further heating the sampling chamber; and evacuating the sampling chamber and the analysis device using the vacuum.

13. The method of claim 12, wherein the molecule collector comprises a Carboxen® coated mesh.

14. The method of claim 12, wherein ablating VOCs off of the molecule collector further comprises ablating lighter and/or less bound VOCs first and then ablating heavier and/or more strongly bound VOCs later.

15. The method of claim 14, further comprising ablating lighter and/or less bound VOCs first and then ablating heavier and/or more strongly bound VOCs later, by varying tuning of the laser's frequency and/or intensity.

16. The method of claim 14, wherein the analysis device first identifies one or more lighter and/or less bound target VOCs ablated off of the molecule collector first and later identifies one or more heavier and/or more strongly bound target VOCs ablated off of the molecule collector later.

17. The method of claim 12, wherein the analysis device comprises a mass spectrometer, a computing device communicatively coupled to the mass spectrometer, and an output device communicatively coupled to the computing device, and wherein the identifying the one or more target VOCs comprises:

ionizing, by an ionizer of the mass spectrometer, at least the portion of the VOCs released from the molecule collector to produce one or more ionized fragments;

separating, by a mass analyzer of the mass spectrometer, the one or more ionized fragments;

identifying, by a detector of the mass spectrometer, the one or more target VOCs based on the separated one or more ionized fragments, wherein the output representative of the one or more target VOCs is generated, by the computing device, based on information associated with the one or more target VOCs identified by the detector; and displaying the output at the output device.

18. The method of claim 12, wherein the analysis device comprises a Terahertz (THz) spectrometer, and wherein the identifying the one or more target VOCs comprises:

emitting, by an excitation source, an excitation signal within the sampling chamber subsequent to the release of at least a portion of the VOCs from the molecule collector; and identifying, by a detector of the THz spectrometer, the one or more target VOCs based on one or more characteristics associated with excitation of at least the portion of the VOCs released from the molecule collector in response to the excitation signal.

19. The method of claim 18, wherein the excitation source comprises a THz laser.

20. The method of claim 18, wherein the one or more characteristics associated with the excitation of at least the portion of the VOCs comprise at least one of: an absorbance characteristic and a fluorescent emission.

21. The method of claim 12, wherein the one or more target VOCs include:

metabolites, metabolite markers, ketones, aldehydes, or a combination thereof indicative of SARS-CoV-2 and/or Coronavirus Disease 2019 (COVID-19) caused by SARS-CoV-2; and/or Δ-9-THC, 11-hydroxy-tetrahydrocannabinol (11-OH-THC), carboxy-tetrahydrocannabinol (THCCOOH), THC metabolites, opioids, opioid metabolites, or a combination thereof.

22. A non-transitory computer-readable storage medium storing instructions that, when executed by one or more processors, cause the one or more processors to perform operations for analyzing a breath sample, the operations comprising:

activating a laser configured to ablate volatile organic compounds (VOCs) present within a sampling chamber subsequent to a breath sample being provided to the sampling chamber, the sampling chamber comprising a molecule collector disposed within the sampling chamber, and the molecule collector configured to adhere VOCs present in the breath sample;

concurrent with activating the laser, introducing a vacuum in an analysis device;

identifying, using the analysis device, one or more target VOCs from among the VOCs present in the sampling chamber subsequent to release of at least a portion of the VOCs from the molecule collector, wherein at least the portion of the VOCs are released from the molecule collector by the laser ablating VOCs present within the sampling chamber;

generating an output representative of the one or more target VOCs, wherein the output representative of the one or more target VOCs comprises information that quantitates a concentration of the one or more target VOCs with respect to a source of the breath sample; and concurrent with at least generating the output representative of the one or more target VOCs, cleaning the sampling chamber by:

further heating the sampling chamber; and evacuating the sampling chamber and the analysis device using the vacuum.

* * * * *